United States Patent
Kumakhov

(10) Patent No.: US 6,271,534 B1
(45) Date of Patent: Aug. 7, 2001

(54) DEVICE FOR PRODUCING THE IMAGE OF AN OBJECT USING A FLUX OF NEUTRAL OR CHARGED PARTICLES, AND AN INTEGRATED LENS FOR CONVERTING SUCH FLUX OF NEUTRAL OR CHARGED PARTICLES

(76) Inventor: Muradin Abubekirovich Kumakhov, Novikova-Priboya 5/2, 24, Moscow (RU), 123103

(*) Notice: Subject to any disclaimer, the term of this patent is extended or adjusted under 35 U.S.C. 154(b) by 0 days.

(21) Appl. No.: 09/128,467

(22) Filed: Aug. 4, 1998

Related U.S. Application Data

(63) Continuation-in-part of application No. 08/605,148, filed on Mar. 1, 1996, now abandoned.

(30) Foreign Application Priority Data

| Jul. 8, 1994 | (WO) | PCT/RU94/00146 |
| Jul. 27, 1994 | (WO) | PCT/RU94/00168 |
| Aug. 11, 1994 | (WO) | PCT/RU94/00189 |

(51) Int. Cl.$^7$ .................................................. G02B 5/124
(52) U.S. Cl. ......................................................... 250/505.1
(58) Field of Search ........................... 250/505.1; 378/49; 313/103 LM, 105 LM

(56) References Cited

U.S. PATENT DOCUMENTS

| 5,016,267 | 5/1991 | Wilkins . |
| 5,115,130 | 5/1992 | Suzuki et al. . |
| 5,175,755 | 12/1992 | Kamakhov . |
| 5,192,869 | 3/1993 | Kamakhov . |
| 5,239,568 | 8/1993 | Grenier . |
| 5,479,469 | 12/1995 | Fraser et al. . |
| 5,497,008 | 3/1996 | Kumakhov . |
| 5,604,353 | 2/1997 | Gibson et al. . |
| 5,744,813 | * 4/1998 | Kumakhov ..................... 250/505.1 |

FOREIGN PATENT DOCUMENTS

| 92/08235 A1 | 5/1992 | (WO) . |
| 92/09088 A1 | 5/1992 | (WO) . |

OTHER PUBLICATIONS

"Production Automation and Industrial Electronics", Moscow, Sovetskaya Entsiklopediya PH, 1964, vol. 3, p. 277, and vol. 1 1962, p. 209.

"Electronics. An Encyclopedia dictionary", Moscow, Sovetskaya Entsiklopediya PH, 1991, pp. 254–255.

(List continued on next page.)

Primary Examiner—Kiet T. Nguyen
(74) Attorney, Agent, or Firm—McDermott, Will & Emery

(57) ABSTRACT

The device according to a first invention is adapted for producing the image of an object with the aid of radiation that either has been transmitted therethrough or excited therein or else scattered thereby. It contains an integrated lens, which is placed between a radiation source and a means for placing the object, or between the latter means and an image-forming means (that registers the distribution of intensity of the radiation incident thereon) (or else in both of these spaces). The integrated lens is the package of sublenses of a various degree of integration, wherein the sublens of the least degree of integration represents the package in a common envelope of radiation transporting channels in form of microcapillary tubes, which is growing out of their drawing and reduction together with an envelope at the temperature of softening of their material, the sublens of each higher degree of integration represents the package in a common envelope of the sublenses of the previous degree of integration, which is growing out of their drawing and reduction together with an envelope at the temperature of softening of their material, all sublenses of the highest degree of integration are composed in a unified structure which is growing out of joint forming at the temperature of softening of their material, and the channels of radiation transporting, with the exception of the channels.

25 Claims, 14 Drawing Sheets

OTHER PUBLICATIONS

"Physics of Image Visualization in Medicine" The Physics of Medical Imaging Edited by Steve Webb, Russian Translation published in Moscow, Mir PH, 1991, pp. 41, 101, 134.

"X–Ray Microscopy" X–Ray Optics and Microscopy. Edited by G. Schmahl and D. Rudolph, Moscow, Mir PH, 1987.

"The Physics of Medical Imaging" Medical Science Series. Edited by Steve Webb, no dated.

* cited by examiner

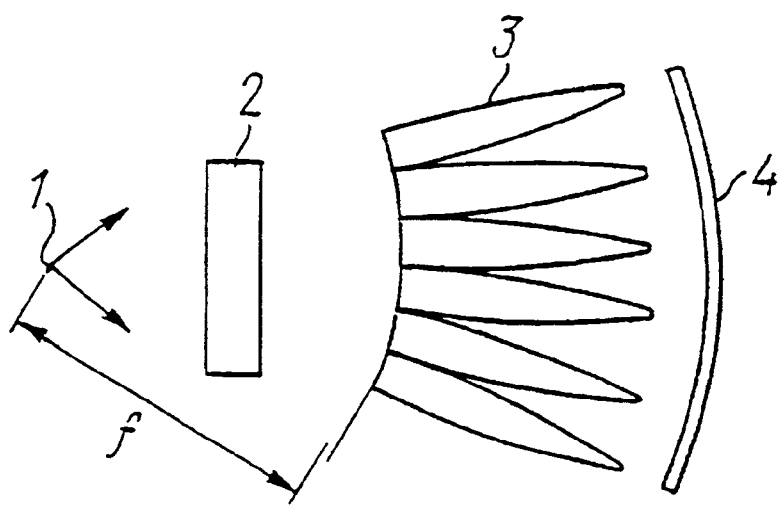
FIG. 4
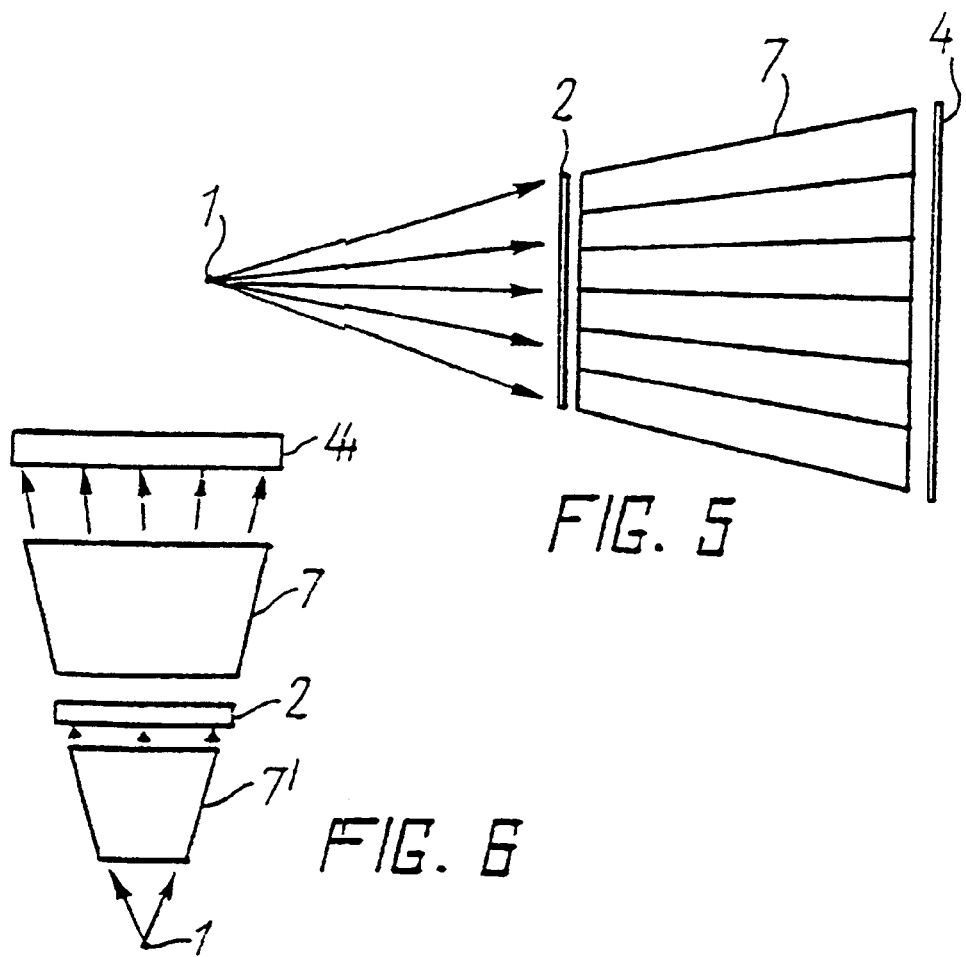
FIG. 5
FIG. 6

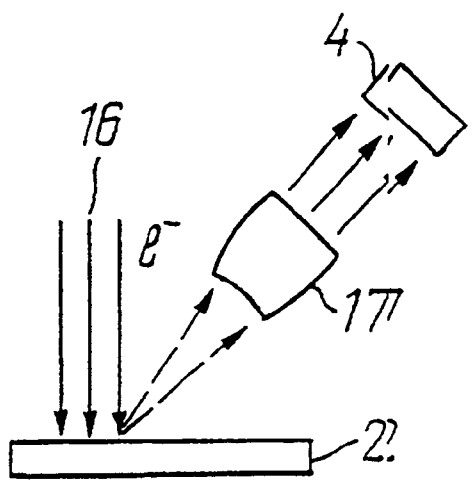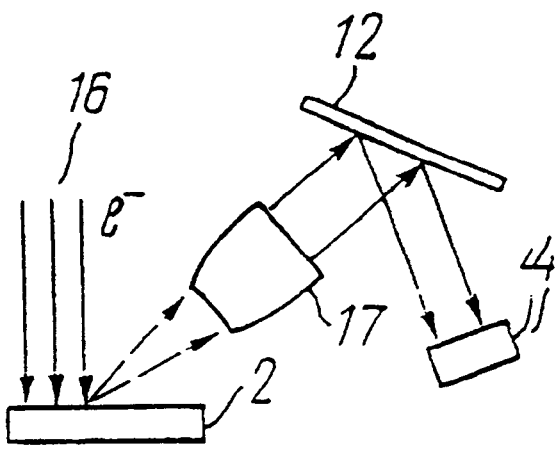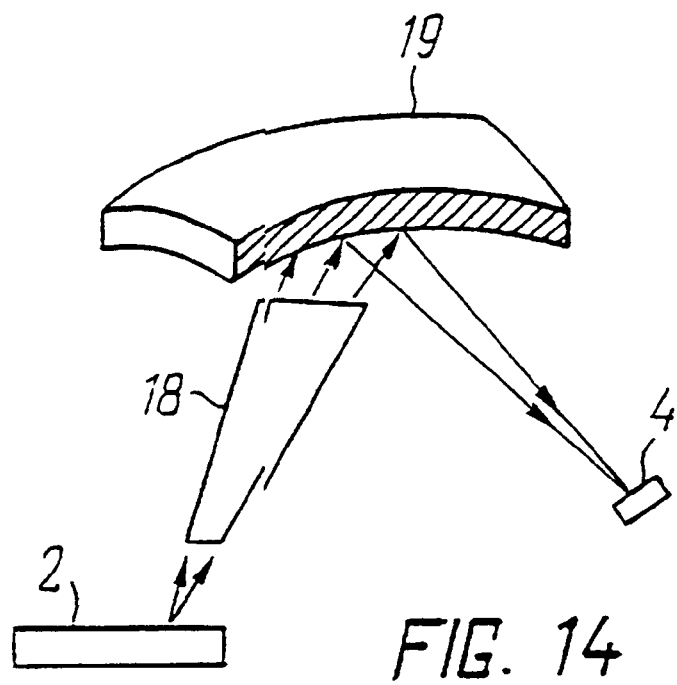

DEVICE FOR PRODUCING THE IMAGE OF AN OBJECT USING A FLUX OF NEUTRAL OR CHARGED PARTICLES, AND AN INTEGRATED LENS FOR CONVERTING SUCH FLUX OF NEUTRAL OR CHARGED PARTICLES

RELATED APPLICATIONS

This application is a continuation-in-part of U.S. application Ser No. 08/605,148, filed Mar. 1, 1996, now abandoned which claims priority of International Application Nos. PCT/RU94/00189, filed Aug. 11, 1994; PCT/RU94/00146, filed Jul. 8, 1994; and PCT/RU94/00168, filed Jul. 27, 1994.

FIELD OF INVENTION

The present invention relates to imaging an object by radiation methods when studying an object or forming a pattern corresponding to the structure of a preset configuration of an object, and to controlling the flux of neutral or charged particles, namely, for bending the beams of such particles, focusing these beams, transforming a diverging radiation into a quasi-parallel one, and vice versa, filtration and monochromatization of said radiation, separation of particles differing in energy, etc., both during the process for producing the image of an object and when solving other problems encountered in medicine, nuclear physics, analytical instruments, etc.

BACKGROUND OF THE INVENTION

It is known the methods for studying various objects involving formation of an image of the object's structure by exposure of the objects to a flux of neutral or charged particles (neutrons, electrons, gamma-quanta, X-rays, etc.), and registering the distribution of the radiation intensity resulting from interaction with the object. The thus-formed image is interpreted as the distribution of interaction properties between the object and the radiation used, these properties being inherent in the various elements of the object, in particular, as a two-dimensional projection of a spatial distribution of attenuation of the radiation resultant from the transmission through the object (cf. the textbook *Production Automation and Industrial Electronics* (Moscow, Sovetskaya Entsiklopediya PE, 1964, v. 3, p. 277, v 1, p. 209 (in Russian))

Similar methods are also known in electrons, X-ray, and other types of lithography for forming a preset pattern corresponding to a known structure of a specially made object (i.e. stencils mask); (cf. e.g., Electronics: *An Encyclopedic Dictionary.* (Moscow, Sovetskaya Entsiklopediya PE, 1991, pp. 254–255 (in Russian)).

The above methods are performed by devices, having a radiation source, a means for placing an object such that it may be exposed to the radiation such as a holder, and a means for image recording which is sensitive to radiation resulting from the interaction of the source-emitted radiation and the object such as a detector.

However, capabilities of said methods are limited unless use is made of a means for controlling a primary particle flux or a flux resulting from interaction with the object. In particular, there is a need for controlling the spectrum, direction, width, divergence, and other beam parameters of the radiation beam.

Some prior-art radiation methods for producing the image of an object are known to use the concept described before are performed with the aid of optical elements which are capable of solving some of the problems mentioned before, in particular, controlling the beam width and selecting the particles that have deviated from a preset direction (cf. *Physics of Image Visualization in Medicine*, edited by S. Webb, the Russian translation published in Moscow (Mir PE, 1991, pp. 41, 101, 134)). Setting aside the fact that the problems thus solved bear a specific nature, it is also worth noting that the concepts used in these methods involve the use of a radiation source having surplus intensity Use of other types of optics in the devices of the character discussed herein is addressed in the symposium "X-ray Optics and Microscopy", edited by G. Schmahl and D. Rudolph (Moscow, Mir PE, 1987), wherein there are considered, in particular, use of Fresnel zone plates for beam focusing (id. at p.87), and grazing-incidence mirror optics (id. at p. 174). However, Fresnel zone plates are characterized, due to the specific features of the physical concept applied, by an extremely high selectivity as for particle energy (wavelength), and for this reason such plates cannot be used for controlling a broad-spectrum radiation. In addition, as is noted in the symposium text, these plates should have a very small size and the devices making use of these plates feature a small angular aperture and a low aperture ratio. As far as mirror optics is concerned, while these optics have practically acceptable geometric dimensions, they are capable, as a rule, of only a single reflection, this being due to extremely low magnitudes of the angle of total external reflection effective for the radiation of the ranges under discussion. Thus, the devices that make use of such optics feature only restricted possibilities for controlling radiation beams, as well as an extremely small angular aperture which corresponds to too low magnitudes of the angle of total external reflection.

One more prior-art device for producing the image of an object (U.S. Pat. No 5,175,755 issued Dec. 29, 1991) is of another design. This device makes use, for controlling a radiation beam, of an optical system which appears as a lens established by a set of channels having reflecting walls and which is adapted for radiation transport. A variety of modes of controlling a flux of particles are provided in the device. In particular, the transformation of a divergent radiation into a quasi-parallel one before exposing an object to the radiation, transporting a broad-spectrum radiation in conjunction with a possibility of cutting-off the hard radiation component, and transforming the size of the resultant image.

U.S. Pat. No 5,192,869, issued Mar. 9, 1993 discloses the construction of a lens for transforming a flux of neutral or charged particles which can also be used for controlling a flux of particles and is also suitable for use as a component part of a device for producing the image of an object. The lens makes use of rigid supporting elements spaced apart from one another lengthwise so as to provide a rigid fixing of the channel-forming elements at places where they pass through holes in the supporting elements. An appropriately selected arrangement of the holes enables the attainment of the correspondence of the axial lines of individual channels to the generating surfaces of a required shape. In order to meet the condition of the radiation transport along the channels without a considerable loss, the cross-sectional dimensions of each individual channel must be as small as possible. However, the aforementioned construction, involving the use of a mechanical assembly procedure, sets limits on the minimum channel cross-sectional dimension. In particular, with radiation transport channels made of glass capillaries or polycapillaries having a diameter on the order of 300 microns, the glass tends to lose the properties required for proper assembling. Thus, the capillaries or polycapillaries start "soaring" in the air. They cannot be given a required radius of curvature during assembling, and the capillaries are liable to sag between the points of support. Such a restriction for their diameter results in the radiation losing the ability to focus into a spot having a diameter smaller than the capillary inside diameter or the polycapillaries outside diameter. The least focal spot diameter attainable with such lenses is 0.5 mm, which means that it is impossible to provide a high concentration of radiation due to too large a focal spot diameter.

A finite size of the channels imposes limitation on the range of energies used. With a preset focal length f, even though the radiation source is point-like, a minimum angle of radiation incident on the capillary peripheral zone is $\theta=d/2f$, where d is the channel diameter.

To provide an efficient radiation transfer, it is desirable that the parameter $\theta$ approximate or even be less than the critical angle of reflection $\theta_c$ because the critical angle decreases as the energy increases This condition restricts the use of high energies in lenses of first and second generations For instance, with an X-ray energy E=10 keV, radiation capture into the channel is not in excess of 15%, and, with an increase in the focal length, the capture angle decreases, and hence the efficiency of the system decreases, too. It follows that it is necessary to use radiation transfer channels having cross-sectional dimensions of microns and submicrons This is impossible, due to the aforementioned reasons, with the construction described before and involving the use of mechanical assembling during the manufacture.

Mechanical assembling is also the cause of another disadvantage. Angular divergence is determined by the expression $\Delta\theta=\Delta L/L$, where $\Delta L$ is the sum of variations of capillary diameter and the diameter of a hole in the support disk, L is to the distance between the disks which is not to exceed 1–3 cm. With a $\Delta L$ being about 10% of the diameters and the value of the L on the order of 500 microns, $\Delta\theta$ is on the order of $5 \cdot 10^{-3}$ rad which is typically unacceptable.

The aforedescribed device and lens as taught in U.S. Pat. Nos. 5,175,755 and 5,192,869, respectively, have capabilities which are restricted, apart from the factors mentioned before, also by the fact that they utilize only the channeling properties of individual channels functioning independently of one another. In this case, the wave properties of the particles being channeled are exhibited only when the particles are reflected from the channel walls during their transfer along the channels. This is due to the fact that no measures are taken in the lens construction for displaying the effect of interaction between particles after their having been transferred along the different channels. This limits the attainable degree of radiation concentration to the geometric accuracy of the orientation of the channels towards a desired point. It also precludes energy separation of particles, and thus monochromatization of the radiation with the aid of the lens itself, in the absence of any other means.

The restrictions stated above affect adversely the capabilities of the device for producing the image of an object which has an optical system in the form of a lens built up of a set of channels having reflecting walls for radiation transfer In particular, these restrictions preclude any increase in the resolution of the devices reduction of the radiation load that the object under examination is exposed to, and the use of a lower-power radiation source.

SUMMARY OF THE INVENTION

The present invention is aimed at increasing the efficiency of utilization of radiation in the form of a flux of neutral or charged particles for producing an image appearing as the distribution of intensity of the radiation after its interaction with the object. The obtained technical result resides in a higher resolution in conjunction with a reduced effect of radiation produced on the object, accompanied by an increased intensity of radiation acting on the sensing elements (sensors) of an image-forming means. The aforesaid factors acting jointly contribute to an extended range of possible media under examination and of those serving as carriers of the resultant image.

As far as a lens for converting a flux of neutral or charged particles is concerned, the present invention is aimed at increasing the attainable degree of radiation concentration, including concentration of radiation corresponding to different wavelengths of an input flux in various spatial regions. The construction of the lens in the present invention over comes the adverse effect of technological restrictions inherent in prior lenses.

Furthermore, the invention provides for other technical advantages of a variety which are partially the subject of a detailed description that follows.

The present device for producing the image of an object has a source of radiation in the form of a flux of neutral or charged particles, a means for arranging an object with a possibility of it being exposed to the effect of radiation generated by this source such as a holder, a means for image formation providing a possibility of recording the distribution of intensity of the radiation after its interaction with the object such as a detector, and an optical system, which incorporates at least one lens aimed at converting a flux of particles. The lens is interposed between the radiation source and the means for placing the object, or between the latter means and the means for image formation, and this lens is established by a set of channels for radiation transfer, having reflecting walls. Unlike prior devices, the present device features, for example, all or part of the channels establishing the lens for converting the flux of particles arranged in an orderly fashion across the lens, and having axial symmetry.

In this case there may be observed, for all the channels arranged orderly across the lens, in particular, a condition of mirror symmetry with respect to one or two mutually perpendicular axes of the lens cross-section. An ordered arrangement of the channels, observing a central or rotational symmetry with respect to the lens' longitudinal axis, is also possible.

It is partially the due observance of symmetry that makes possible a coherent interaction between equal-energy particles emitted by the radiation source and, after having passed through the lens, and coming along various paths, at the same space point of convergence, as well as the onset of interference phenomena, which lead ultimately to the aforementioned technical result.

A particle flux converting lens (or any of such lenses making part of the optical system, if a number of the lenses are made use of) can be established by snugly positioning sublenses whose total cross-section is variable along the length of the lens in accordance with a required longitudinal profile thereof. Sublenses (lenses with the smaller cross-sectional sizes, i.e. the modules, of which consists the lens), in turn, can consist of some more smaller sublenses. Therefore offered lens as a whole, which is joint combination of sublenses, can be called as an integrated lens. In relation to sublenses included in a lens structure it can be spoken about a various degree of integration. The highest degree of integration is inherent in sublenses, which immediately will derivate an integrated lens. The sublenses, of which these sublenses immediately consist, have a degree of integration per unit of 1 lower, etc. The least degree of integration have the sublenses derivated immediately by capillary tubes, being channels of transporting of radiation Such construction of the lens makes it possible to dispense with the need for use of supporting elements as means forming the longitudinal lens profile and determining the shape of the lens channels, and eliminates restrictions inherent in mechanical assembling involving the use of such supporting elements.

The most efficient is such a device wherein the sublenses are arranged in an orderly fashion across the lens in keeping with axial symmetry. In particular, the integrated lens can consist of sublenses, which will derivate several coaxial layers.

An increased efficiency of radiation focusing, which is the most important result of the aforedescribed embodiment of a lens or lenses making part of the present device for producing the image of an object, promotes both higher resolution and radiation intensity in the zone of the location of the image formation means. While high enough for the image to record, and it also contributes to a lower intensity of radiation that the object is exposed to.

According to an embodiment of the present device, the image formation means is so arranged as to make it possible to transfer thereto the radiation that has passed through the object.

In one of such cases, the optical system has a number of asymmetric lenses, each of which is capable of reducing the image being generated. These asymmetric lenses are interposed between the means for placing the object and the means for image formation in such a manner that each of the asymmetric lenses transfers the radiation from the object elements nearest to the lens entrance end, and all of the asymmetric lenses enables the production of a mosaic image of the object. With such an embodiment of the device the dose of radiation that the object and the means for placing the object sees may be lessened.

A source of diverging radiation may be made with a possibility of forming two characteristic $K_\alpha$ spectral lines. In this case, the optical system has also a rotary filter-window placed either before or after the lens or hemilens aimed at forming a quasi-parallel beam. The filter-window incorporates two alternating sectors, each aimed at suppressing the radiation of either of the $K_\alpha$ spectral lines. The lens or hemilens mentioned above features its longitudinal axis having a bend intended to cut off the hard radiation component. Alternatively, it has a straight longitudinal axis, in which case a set of parallel capillaries is placed before the object in order to cut off the hard radiation component. Such being the case, there are formed periodically two images corresponding to the interaction between the object and the particles having the energy corresponding to the $K_\alpha$ spectral lines, thus providing prerequisites for forming a final image by subtracting one of the two images from the other. This makes it possible to enhance the degree of clarity of the image due to the suppression of the interfering background.

In a further particular case, also characterized by the use of a diverging radiation source involving a possibility of forming two characteristic $K_\alpha$ spectral lines, the optical system has two lenses or hemilens for forming quasi-parallel beams arranged at an angle to each other, and two crystal monochromators for discriminating either of the $K_\alpha$ spectral lines, these crystals being positioned past the lenses or hemilenses with a possibility of reflect is exposed to is reduced in direct proportion to the degree of reduction of the image size and the amount of focusing of the radiation emerging from the asymmetric lenses.

According to another embodiment, an optical system has an image-enlarging diverging hemilens interposed between the means for placing the object and the image forming means, this hemilens being made up of conical capillaries or polycapillaries. The radiation source may be positioned at the focal point of the diverging hemilens or on its optical axis in an out-of-focus position. In the latter case, there is provided energy filtration of the captured particles. With the same purpose in view, when using a finite-size radiation source having an exit aperture shaped as a circle, the central portion of the latter can be shielded.

The optical system in the embodiments considered, characterized by the provision of a conical diverging hemilens for image enlarging, may also have a second diverging hemilens made up of conical capillaries or polycapillaries and having a smaller size in cross-section as compared with the first one, this second hemilens being interposed between the radiation source and the means for placing the object. This feature enables the production of an image having adequate dimensions and the reduction of the object exposure dose.

In the aforedescribed particular cases, the object is exposed to a directly diverging radiation generated by the source. According to another embodiment, the optical system has a lens or hemilens for forming a quasi-parallel beam of particles which is interposed between the radiation sourcing monochromatized beams towards the means for placing the object. The device also has a second means for image forming, each of the image-forming means being located past the means for placing the object with a possibility of receiving the radiation reflected from one the crystal monochromator s after its having passed trough the object. The device thus embodied is also capable of forming two images corresponding to different $K_\alpha$ spectral lines.

In a yet further particular embodiment of the device, the optical system has a lens positioned between the radiation source and the means for placing the object, this lens capable of focusing the radiation inside the object in order to produce the image of its element whereon focusing is performed In this case, the radiation source, the lens, and the means for image-forming are capable of a joint rotary motion with respect to the means for placing the object without affecting their mutual arrangement and that of the radiation focusing point, this point being the center of the rotary motion. Such a construction arrangement makes it possible to concentrate the radiation at the same element of the object throughout the entire observation time without irradiating, during the period of observation, the same elements surrounding the one under observation. It is due to this feature that said elements are exposed to radiation alternately, that is, during only a part of the observation time, and at a lower radiation concentration than the element under observation.

According to another embodiment of the present device, the image-forming means is so positioned as to make possible the transferring thereto of the secondary radiation that has been either scattered or excited in the substance of the object as a result of the interaction between the substance and the radiation generated by the source.

In a related embodiment, the radiation source is capable of forming a flux of electrons or ions for exciting a secondary X-ray radiation in the substance of the object, and the optical system has a hemilens adapted for transferring the secondary radiation to the image-forming means and is capable of scanning the object with its focal point.

In another related embodiment, the optical system has a lens for transferring the radiation generated by the source to the object, and a lens for transferring the secondary radiation to the image-forming means, both of these lenses having a common focal point and being jointly movable for scanning the object with their common focal point.

In both of the aforesaid particular embodiments, a means for beam monochromatization may be interposed between the lens for transferring the secondary radiation to the image-forming means and the latter means, this monochromatization means being provided, in particular, as a doubly curved crystal.

A polarizing target may be interposed adjacent to the lens for transferring the radiation to the means for placing the object, this target being capable of changing the direction of the beam reflected therefrom by 90° with respect to the beam incident thereon. The polarizing target may be in the form of a crystal monochromator.

According to a particular embodiment of the device, wherein provision is made for confocal lenses of which one transfers radiation to the means for placing the object and the other transfers the secondary radiation therefrom, the latter lens may have radiation transfer channels symmetrical with respect to the optical axis and a focal point situated in the space between the lens exit end and the image-forming means. A microaperture may be provided in the space with a possibility of scanning the image of the object.

Such a construction arrangement enables the device to be used for an elementary analysis of a sample serving as an object. The device can thus be 'tuned' to a specific value of energy of the secondary-radiation particles by positioning the microaperture on the lens optical axis. the lens transferring the secondary radiation, with displacement out of focus corresponding to the energy E of the particles by the following value:

$$\Delta f = f \cdot \Delta E / E,$$

where f is the focal length corresponding to the energy E, and $\Delta E$ is the required resolution value with respect to the energy E.

In order to suppress the background developed by the second radiation with the energies that are of no interest, those areas of the lens cross-section, over which the particles having such energies are mostly propagated, can be closed on the lens exit with a circular (when the central lens portion is involved) or an annular (in the case of the lens layers removed from its axis) radiation-tight shield.

In a further particular embodiment which provides image production with the aid of Compton radiation scattered by the object, the optical system has a lens positioned between the radiation source and the means for placing the object and is adapted for forming a quasi-parallel beam. In this case, a collimator, appearing as a system of straight capillaries, is interposed between the means for placing the object and the image-forming means. The radiation source, the lens, the collimator, and the image-forming means are situated in the same half-space with respect to the means for placing the object.

In a yet further embodiment, wherein the image of an object is produced with the aid of Compton radiation scattered by the inner elements of the object, the optical system has a lens interposed between the radiation source and the means for placing the object and is adapted for focusing the radiation inside the object, and a collimator in the form of a system of conical capillaries, this collimator being focused at the same point as the lens. The collimator is interposed between the means for placing the object and the image-forming means, while the lens, the collimator, and the image-forming means are situated in the same half-space with respect to the means for placing the object and are jointly movable with respect thereto without changing their mutual arrangement, whereby the object can be scanned with a common focus of the lens and collimator.

In both of the particular embodiments mentioned above, the fact that all the elements of the device are located in the same half-space with respect to the means for placing the object enables one to examine an object accessible only unilaterally.

A further particular embodiment of the device makes use of both the radiation transmitted through the object and that scattered by its internal elements. With this purpose in view, the device has a source of plane-polarized radiation, and the optical system incorporates a lens built up of square capillaries having similarly oriented walls and the like is interposed between the radiation source and the means for placing the object The lens is being capable of focusing the radiation inside the object. In addition, the optical system has another lens composed of conical capillaries, this lens being located before the image-forming means and having a common focal point with the lens for focusing a plane-polarized radiation. An optical axis of the lens composed of conical capillaries is arranged square with the optical axis of the lens for focusing a plane-polarized radiation in the plane of the vector of magnetic field intensity of the radiation. A possibility is provided for use of one more image-forming means and a lens composed of conical capillaries, both being situated symmetrically with those mentioned above, on the other side of the means for placing the object. The device, according to the specific embodiment under consideration, also has a lens for forming a quasi-parallel beam, the lens being situated on an extension of the optical axis of the lens for focusing a plane-polarized radiation and being confocal therewith, the additional image-forming means being positioned past, the quasi-parallel-beam forming lens In this case, the radiation source, all the lenses mentioned above, and both of the image-forming means are conjointly movable with respect to the means for placing the object without affecting the mutual arrangement of the components, thus making possible, similarly to the preceding embodiment, scanning of the object. Use of both the scattered radiation and the radiation transmitted through the object adds to the scope of information obtained about the object under examination and make it possible, other things being equal, to reduce the exposure of the object.

The herein-described lens for converting a flux of neutral or charged particles, which is an element of the optical system of the device considered hereinbefore in every particular embodiment thereof, is established, by a set of radiation-transfer channels having reflecting walls. All or part of the channels of the present lens are arranged in an orderly fashion across the lens according to, e.g., axial symmetry.

In a particular case, all the channels of the lens may have straight longitudinal axes which may be both parallel and convergent (divergent). In the latter case, the channels are cone-shaped. Interference phenomena, occurring due to orderly and symmetrical arrangement of the channels across the lens, make it possible to focus the emerging radiation from the lens even with the parallel channels which the lens is formed by.

In the particular embodiments of the lens, wherein the channels which the lens is formed of are bent (except, of course, save the central channel), their bend is the same for the channels equally spaced apart from the axis or planes of symmetry of the lens in its longitudinal section. This enables one to meet the condition of an orderly and symmetrical arrangement of the channels in any cross-section of the lens and to provide focusing of the emerging radiation using, not only the guiding properties of the channels forming the lens, but also the interference phenomena occurring in the space wherein the lens emerging radiation propagates (on the base of reciprocity, the lens possesses similar properties when functioning "as receiver", that is, with respect to the diverging radiation emitted by a quasi-point-like source and incident on its exit end the lens may serve as a mean, for forming a quasi-parallel beam). The cross-section of the channels is variable along their length in accordance with a change in the lens cross-section as a whole, whereby the channels can be placed snugly, thus making it possible to eliminate the use of supporting elements when assembling the lens.

When the lens channels are bent, the lens can be shaped as a flare or funnel, a half-barrel, a symmetrical or unsymmetrical barrel, etc.

Whenever the outer side surface of the lens is convex-shaped (in particular, has the shape of a half-barrel, barrel, etc. with the purpose of providing most favorable conditions for interference of the emergent radiation (from the standpoint of efficient focusing), the channels are preferably arranged around the lens' longitudinal axis in layers featuring the same total cross-sectional areas of the channels belonging to the layers. The radii of the bent channels (i.e., all except the central one) decrease in the direction from the lens' longitudinal basis towards the lens periphery. It is an inversely proportional relationship between the bending radius and the number of the layer, counting from the central one located on the lens longitudinal axis, that proves to be most expedient.

Best results are attained when one of the following quantitative relations is observed:

(a) Radii of curvature of all bent channels are not to exceed $$R_c = 2d/(\theta_c)^2,$$

where d is the channel diameter and $\theta_c$ is the critical angle of reflection for the least-energy particles in the spectrum of the radiation being transferred, (b) Radii of curvature of all bent channels have a minimum value of $$R_c = 2d/2(\theta_c)^2,$$

where d is the channel diameter, and $\theta_c$ is the critical angle of reflection for the highest-energy particles in the spectrum of the radiation being transferred, (c) Radii of curvature of all bent channels meets the condition (a) and are inversely proportional to the number of the layer they belong to (when the numbers of layers are counted in the direction from the lens' longitudinal axis towards the periphery thereof).

The channel curvature may also vary lengthwise the lens, in particular, may be monotonically variable.

The channels may have a helical surface, which promotes controlling a polarized radiation. It is practicable for a lens having such channels that all its channels feature the same helicity, or alternatively that the channels of the various groups have opposite helicity.

As already it was noted, the assemble procedure of the lens can be facilitated, and its accuracy be enhanced, when the lens is made up of similar sublenses arranged in an orderly fashion in the lens cross-section with due observance of an axial symmetry.

In all the embodiments of the lens mentioned before, the channels may be established, in particular, by the inner walls of glass capillaries.

In all particular embodiments of the lens, the inner walls of its channels can be provided with coatings having at least one layer and establishing, together with the walls themselves, a multilayer structure, wherein its adjacent layers have different electromagnetic properties. Moreover, the interface between at least two adjacent media may be in another phase state compared with their base layer. This makes it possible, when channeling the particles, to use, not only the phenomenon of multiple reflection, but also diffuse and potential scattering. This contributes to an increase in the angle of radiation capture and improves the channeling of charged particles (when the coating is electrically conducting and superconducting) and of neutral particles (when the coating appears as a magnetic layer), etc.

There may be applied diffraction structures having one or more periods to the inner walls of the channels, which makes it possible, using the lens, to monochromatize the radiation incident on us entrance and to divide the radiation into fluxes corresponding to the various spectral lines (when the coatings are applied as diffraction structures having several periods), etc.

According to the various embodiments, the lens may be a set of sublenses, in particular, placed snugly and having a total cross section variable lengthwise across the lens according to the longitudinal profile thereof The lens may have, apart from the channels orderly arranged across it, also randomly arranged channels, and the latter channels may even outnumber the orderly arranged ones.

BRIEF DESCRIPTION OF THE DRAWINGS

FIG. 4 illustrates producing a mosaic image of an object using a source of diverging radiation and a system of reducing asymmetrical lenses;

FIG. 5 illustrates producing an enlarged image of an object with the use of a diverging radiation source and a conical hemilens;

FIG. 6 illustrates producing the image of an object with the use of a diverging radiation source, a conical lens for filtering the radiation, and an enlarging conical hemilens;

FIG. 12 illustrates producing the image of an object involving focusing of the image-transferring lens on one of the elements of the object, and irradiating the latter by a flux of particles which excite X-rays;

FIG. 13 is a view of FIG. 12 involving monochromatization of a secondary radiation;

FIG. 14 shows the use of a conical hemilens focused on one of the object elements for transferring the secondary radiation, and an asymmetrically cut doubly curved crystal monochromator;

BEST METHODS FOR CARRYING OUT THE INVENTIONS

The present device is capable of producing a direct-shadow image in the radiation transmitted therethrough, and an image in the form of a distribution of the intensity of radiation scattered by an object or excited in its substance.

When considering the operation, unless it does not affect the correct understanding, the term "object" is employed for the sake of brevity rather than the term "means for placing the object" (inasmuch as when describing the operation of the device, it is essential an interaction between the radiation and the object itself rather than an interaction with the means for its arrangement, though it is the means, and not the object, that proves to be the unit of the device).

Figure 1:
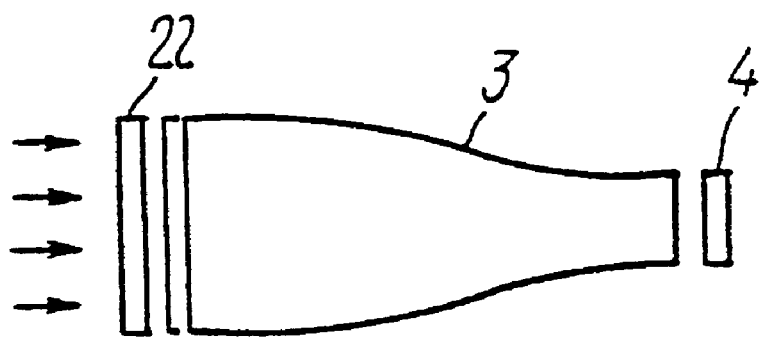
FIG. 1 illustrates producing the image of an object irradiated by a quasiparallel beam of particles, involving the use of a reducing hemilens.

An embodiment of the device is illustrated in FIG. 1, wherein an object 2 is irradiated by a quasi-parallel flux of particles (a means for forming said flux, e.g., a synchrotron, are omitted in the drawing). As used herein, these particles may be neutral or charged. The radiation transmitted through the object 2 is transferred to an image-forming means 4 by an image-reducing hemilens 3. As it has been stated above, this makes it possible to decrease the object exposure dose without reducing the radiation intensity, which becomes practicable due to concentration of the radiation effected when the image size is reduced by the hemilens 3. Used as the means 4 may be any radiation receiver (or detector) that enables one to visualize the image detected (e.g., a film-loaded magazine, an X-ray image intensifier, etc.; cf., in particular, *Physics of Image Visualization in Medicine*, edited by S. Webb (Moscow Mir PE, 1991, vol. 1) (the Russian translation).

When observing the condition $$\theta_1 \leq (d_0/d_1)^2 \theta_2, \quad (1)$$

where $\theta_1$ is the divergence of a quasi-parallel beam, $\theta_2$ is the divergence of the emergent radiation from the hemilens 3, and $d_0$, $d_1$ are the entrance and exit diameters, respectively, of the hemilens 3, the minimum loss in the radiation being transferred is attained. This makes it possible to reduce the power of the radiation source and the object exposure dose.

Figure 2:
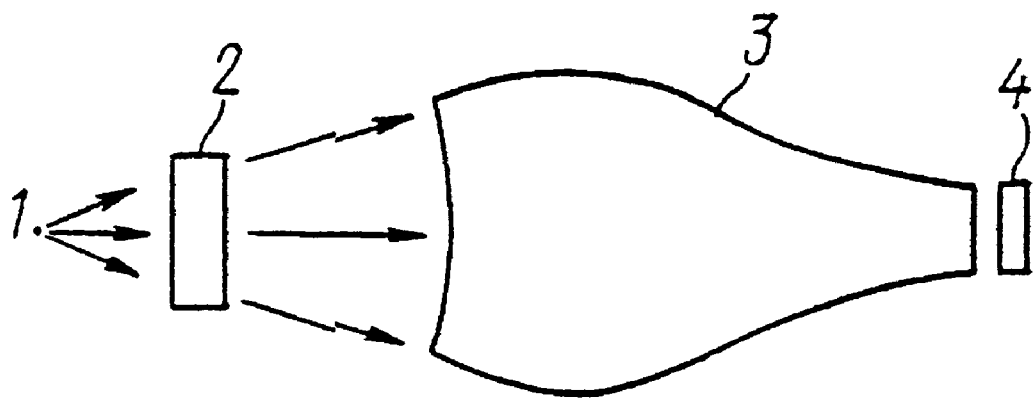
FIG. 2 illustrates producing the image of an object irradiated by a divergent beam of particles with the aid of a reducing asymmetrical lens.
Figure 3:
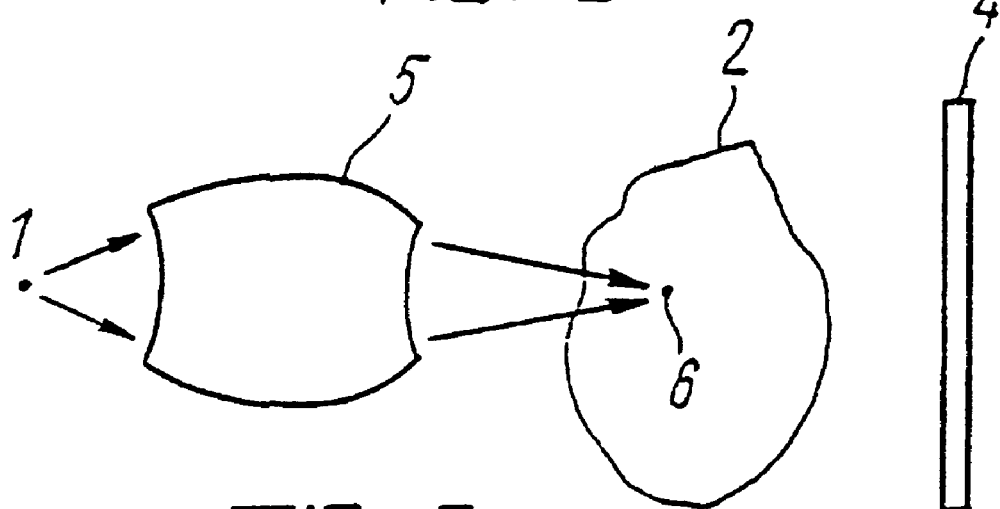
FIG. 3 illustrates producing an enlarged image of an object's inner element using the radiation transmitted through the object.

When the object 2 is exposed to radiation emitted by a source 1 having finite dimensions and generating diverging radiation (see FIG. 2), which, after having passed through the object 2, is transferred to the image-forming means 4 with the aid of the asymmetric lens 3 that reduces, as in the preceding case, the image size, the following condition is to be met $$b/f = (d_1/d_0)\theta_2, \quad (2)$$

where b is the diameter of the exit aperture of the radiation source 1, f is the distance from the radiation source 1 to the object 2, $d_0$, $d_1$ are, respectively the entrance and exit diameters of the asymmetric lens 3, and $\theta_2$ is the divergence of the emergent radiation of the asymmetric lens 3 which is incident on the image-forming means 4.

In order to produce an enlarged image of an inner element 6 of an object 2 the radiation emitted by the source 1 is focused on the element 6 by a lens 5. The image-forming means 4 is, in this case, spaced apart from the object 2 a distance that depends on the desired degree of image magnification.

Information about the object can be obtained in divergent beams. In this case, located past the object 2 is a system of converging lenses 3 (such as hemilens), and situated behind this system is an image-forming means 4 in the form of a mosaic pattern established by the system of hemilenses 3, while the radiation source 1 is located at-the focal point of said system. In this case, the relation (2) must hold true for each of the hemilenses 3. Such an embodiment of the device can find application, in particular, for mammography.

According to one of the embodiments, the image of the object 2 is transferred with the aid of a diverging lens 7 at the focal point of which the radiation source 1 (see FIG. 5) is situated. In this embodiment, the elements of the lens 7 are made up of conical channels that flare up towards the image-forming means 4. Spatial resolution of such an optical system approximates the diameter of the transfer channel at the lens entrance The radiation may be subjected to filtering before the object using a second conical lens 7' located before the object 2. A secondary scattered radiation may be suppressed with the aid of lens 7 (see FIG. 6) This is an improved version of a medical raster.

Figure 7:
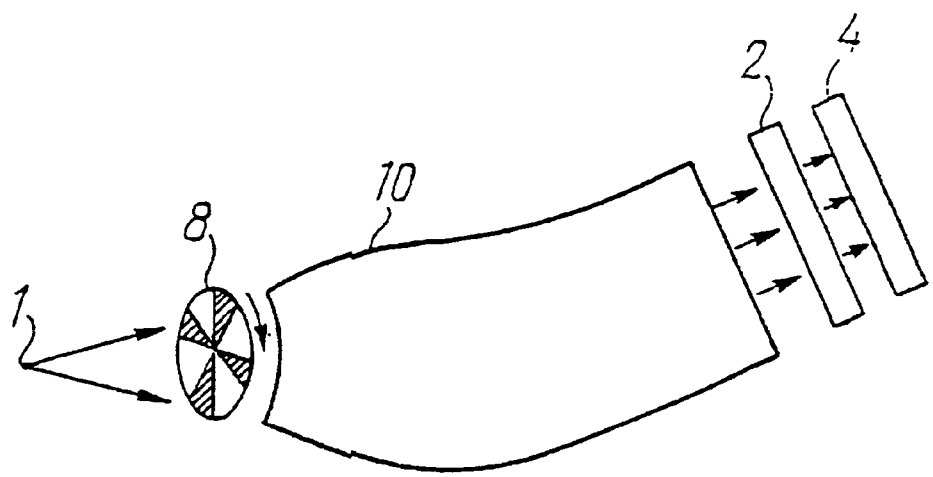
FIGS. 7 and 8 show particular cases of producing alternating images of an object corresponding to two $K_\alpha$ spectral lines, these cases differing in the techniques of cutting-off the hard spectral portion.
Figure 8:
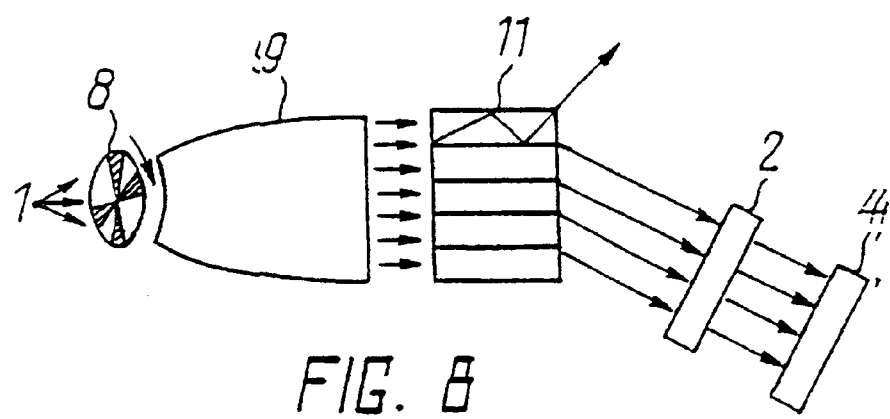
Figure 9:
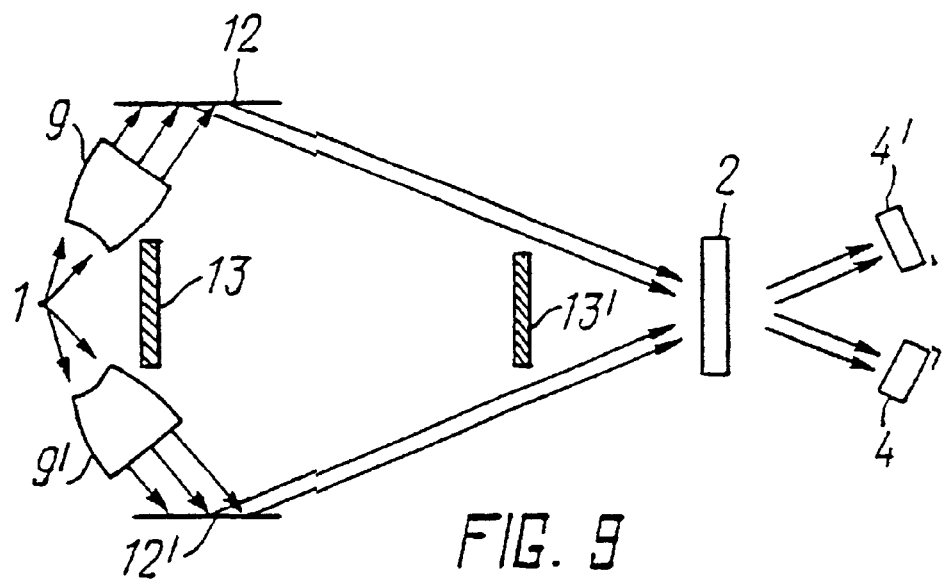
FIG. 9 illustrates simultaneous producing images of an object which correspond to two $K_\alpha$ spectral lines.

A number of embodiments of the proposed device aimed at use predominantly in angiography, is shown in FIGS. 7–9.

In the embodiment of FIG. 7, the radiation source emits photons featuring two Kα spectral lines (in angiography these lines are above and below the line of absorption of iodine, i.e., near 35 keV). A rotary window 8 has a filter which, at one instant, absorbs one of the abovesaid lines and passes the other line, and, at a next instant this reverses its action. The aforesaid window may also be placed past the lens. A lens 10 renders the beam quasi-parallel and at the same time cuts off, due to the presence of a bend therein, the hard radiation component emitted by the X-ray tube.

FIG. 8 shows an embodiment of the device, wherein, used for cutting off the hard radiation component, is a set 11 of parallel capillaries which is located past a hemilens 9 which forms a quasi-parallel beam.

In a further embodiment (see FIG. 9) the image is transferred with the aid of two hemilenses 9, 9', two crystal monochromators 12, 12', and two image-forming means. In this case, one of the $K_\alpha$ spectral lines is transferred and reproduced by means of the crystal monochromator 12 and the image-forming means 4, and the other $K_\alpha$ spectral line is transferred and reproduced, by means of the crystal monochromator 12' and the image-forming means 4'.

Protective shields 13, 13' are provided so that the radiation emitted by the source 1 does not impinge directly on the object 2.

The hemilenses 9, 9' form quasi-parallel beams, while the crystals monochromators 12, 12' provide for monochromatized radiation corresponding to one of the $K_\alpha$ spectral lines. In all the three embodiments discussed before (FIGS. 7–9), another lens may be provided before each of the image-forming means, and may be aimed at reducing the image size and decreasing the patient's exposure dose. In order to attain an efficacious reduction of the exposure dose, the beam divergence $\theta_1$ before the patient should satisfy the condition:

$$\theta_1 = \theta_c (d_1/d_0)^2,$$

where $\theta_c$ is the critical angle of reflection with the energy E=33 keV, and the factor $(d_1/d_0)^2$ is the ratio between the exit and entrance cross-sectional areas of the lens squared.

The two resultant X-ray images (which alternate with each other periodically in the device of FIGS. 7, 8, and exist concurrently in the device of FIG. 9), are processed jointly, using the subtraction method, with the resultant suppressed-background image. The object elements of interest for the operator, such as blood vessels, are then more readily discernible.

Figure 10:
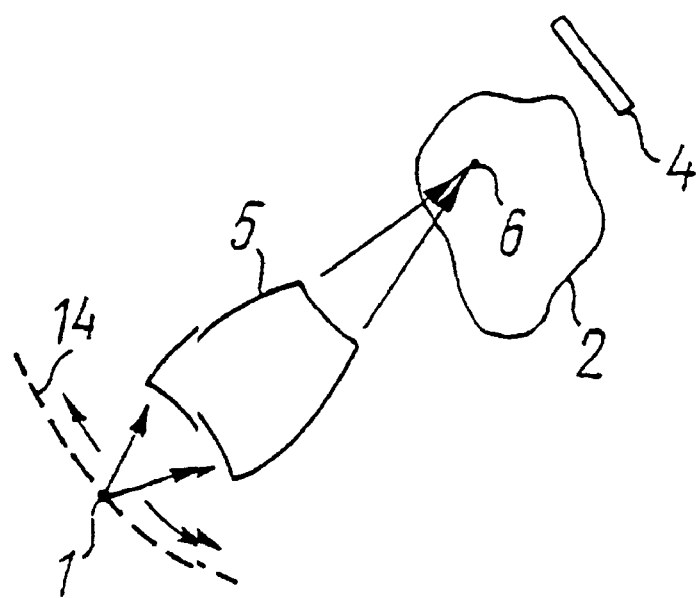
FIG. 10 illustrates producing the image of an inner object element, whereon the source-emitted radiation is focused, without exposure of the same tissues surrounding the element to a constant amount of radiation.

According to one of the practical application of the proposed device, wherein an image is formed with the aid of the radiation that has passed through the object, the radiation is focused on the inner element 6 of the object 2 which is the target of examination, e.g., a tumor (see FIG. 10), using the lens 5. The image-forming means 4 is located on the optical axis of the lens 5 on the opposite side of the object 2. The radiation source 1, the lens 5 and the image-forming means 4 are positioned in a stationary fashion with respect to one another but jointly they may be is rotated about the center, i.e., the point 6 of radiation focusing. The radiation source 1 and the image-forming means 4 are movable over spherical surfaces of the corresponding radii (such a surface 14 for the radiation source 1 being indicated with dashed lines in FIG. 10). It is due to such movement that the radiation is constantly concentrated on, e.g., the tumour 6 whose image is to be produced whereas the tissues surrounding the tumour are exposed to the effect of radiation only for a certain amount of time within the observation procedure.

Figure 11:
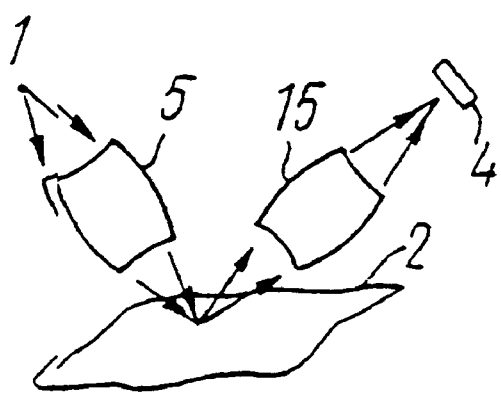
FIG. 11 illustrates producing the image of an object using the object-scattered radiation.

FIG. 11 illustrates an embodiment of the device where, used for image formation is secondary radiation scattered by the object or fluorecence radiation excited therein by the source-emitted radiation. The lens 5 focuses the radiation emitted by the source 1 on one of the elements of the object 2, and a third lens 15, focused on the same elements from the entrance side, transfers the secondary radiation to the image-forming means 4. It is due to the movement of the system of radiation source 1 and the lenses 5, 15 (with their mutual arrangement remaining unaffected) with respect to the object 2, or due to the displacement of the object relative to this system that scanning of the object by a common focus of the lenses 5 and 15 is effected. Thus, it is possible to produce, with the aid of the image-forming means 4, distribution patterns of the object properties that influence the parameters of the secondary radiation. Such geometries is instrumental in both the solution of the locality problem and the suppression of the background resulting from the scattered radiation. This adds to the sensitivity of the method This particular embodiment may be used for locating the position or seating of defects, localizing precisely heavy elements, etc.

FIGS. 12–14 illustrate an embodiment of the device for use in forming, an image of an object with the aid of the radiation excited therein.

Secondary X-rays can be excited in the object 2 (which may be, in particular, a sample or specimen of the material or substance under examination) with the use of an electron or ion beam 16, and this radiation can be collected with the aid of a hemilens 17 (see FIG. 12) on the image-forming means 4.

According to another embodiment of the device (see FIG. 13), the radiation collected by the hemilens 17 is directed onto the monochromator 12 and further onto the image-forming means 4.

The radiation can be efficiently monochromatized using a cone-shaped hemilens 18 and a doubly curved crystal monochromator 19 (FIG. 14).

Two more specific embodiments of the device provide for image production with the use of backscattered Compton radiation.

Figure 15:
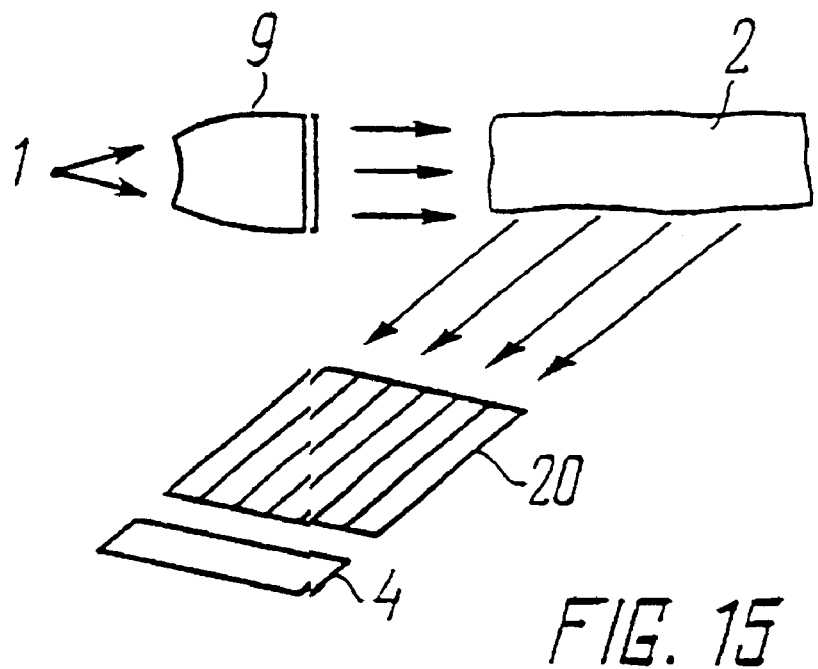
FIG. 15 illustrates producing the image of an object using backscattered Compton radiation.

According to the former embodiment (see FIG. 15) a quasi-parallel beam established by the hemilens 9 (or received directly from a synchrotron source), is directed onto the object 2. Backscattered radiation is incident on the image-forming means 4 through a collimator 20 composed of a system of straight capillaries. In the case when the crystal-monochromator is used as object 2, we obtain essentially new type diffractometer, because use of hemilens increases the intensity of diffracted beam.

Figure 16:
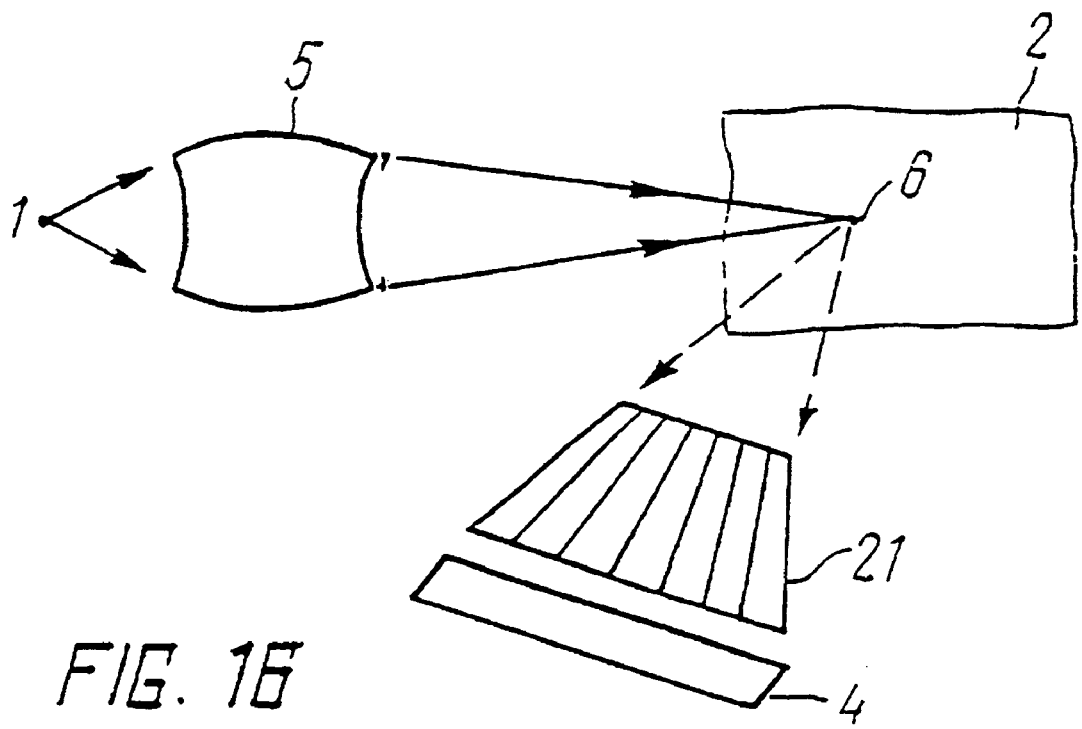
FIG. 16 is a view of FIG. 15 involving focusing the source-emitted radiation on the inner element of the object.

According to the latter embodiment (FIG. 16) the radiation generated by the source 1 is focused by the lens 5 on the object 2. In particular, it is focused on the inner element 6 thereof. A lens 21 composed of cone-shaped capillaries is focused at the same point. The image-forming means 4 is situated beyond the lens 21, depending on the specific situation the object can be scanned by a beam (in which case a system composed of the radiation source 1, the lens 5, the lens 21, and the image-forming means is movable relative to the object as an integral unit). Conversely, the object is movable with respect to the aforementioned components of the device.

In both cases, all the components of the device are located in the same half-space with respect to the object. The means for placing the object may be in the form of a contrivance establishing contact with the object, e.g., a probe jointly movable with the other components of the device relative to the object.

Figure 17:
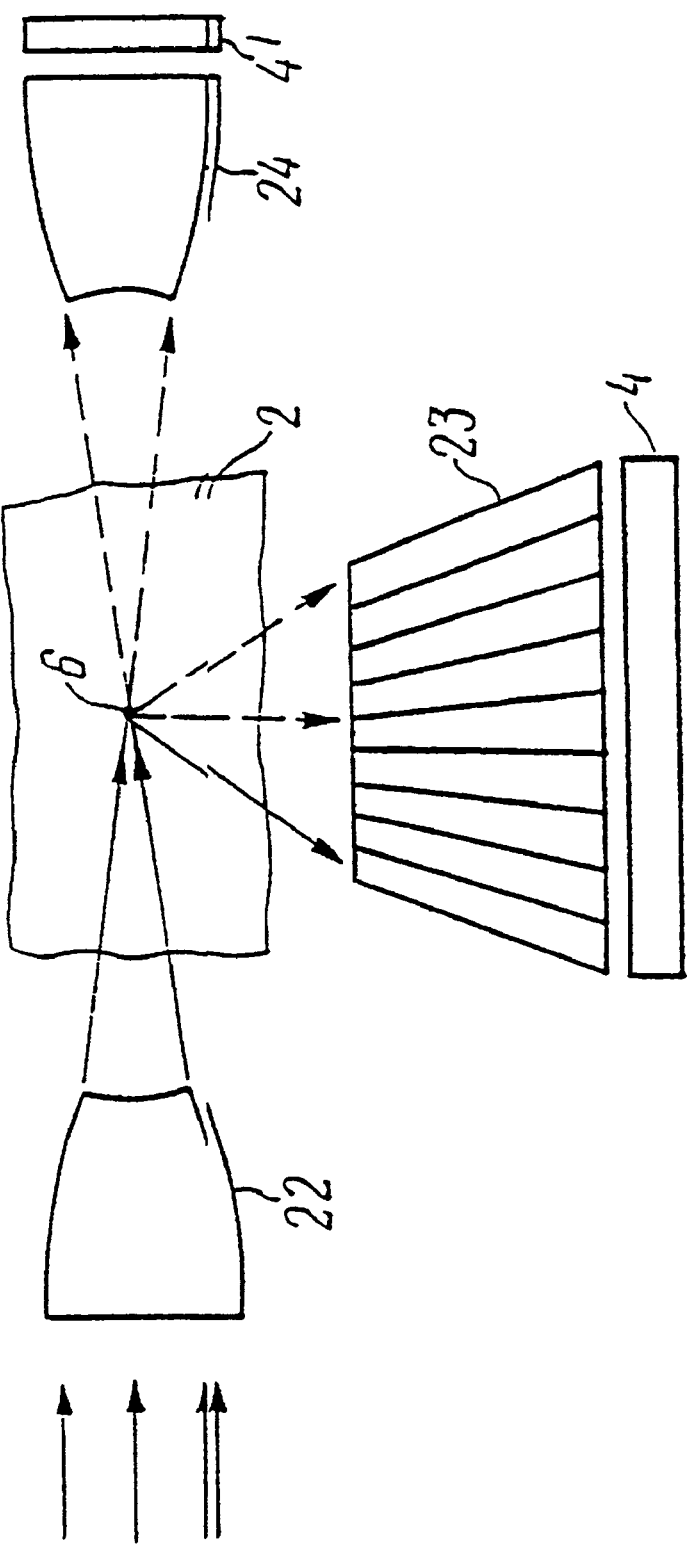
FIG. 17 shows simultaneously producing images of an object, using radiation that has passed through the object and been scattered by it, the object being exposed to plane-polarized radiation.

In order to make an analysis of diverse objects, including for medical diagnosis purposes, efficient use can be made of polarized radiation. A plane-polarized quasi-parallel radiation from, e.g. a synchrotron source, is focused on the inner element 6 of the object 2 by a fourth lens 22 composed of square capillaries having all their walls oriented similarly (FIG. 17). Another lens 24 is conjugate with the lens 22, while the image-forming means 4 is located past the lens 24.

The first and second image-forming means 4 may be situated behind a fifth conical lens 23 whose optical axis is square with a common optical axis of the lenses 23 and yet a sixth lens 24 and is parallel to the vector of a magnetic field generated by the plane-polarized radiation. The conical lens 23 is focused at the same inner point of the object as the lenses 22 and 24. Two images are created in the device according to such an embodiment, one of them being formed by the means 4 using the object-transmitted radiation, and a second image, by the means 4', using the scattered radiation (not shown). Another pair of similar elements may be arranged symmetrically with respect to the lens 23 and the image-forming means 4', which renders the device more informative.

It is worth emphasizing that a possibility of scanning with the lens focal point inside the object opens up fundamentally new possibilities in diagnosing a variety of objects, including new types of medical diagnosis In fact, it may be said to be a new kind of microscopy, wherein the focal point of a source is located inside the object. In addition, geometrical-unsharpness of the image is substantially decreased. Such unsharpness is usually expressed by the following formula:

$$U_r = b d_s / I_1,$$

where b is the size of the object, $I_1$ is the distance from the object to the tube focal point, and $d_s$ is the distance from the object to the detector. When the source is located outside the object the values of $d_s$ and $I_1$, are comparable and the value of $U_r$ approximates that of b, that is the resolution approximates the size of the source. When the lens focal point is spaced very close apart from the defect in the object, the value of d, may be very low and hence the resolution increases. In this case, a fundamentally new increase in the spatial dimensions of the defect under examination.

As has been stated above, axial-symmetry lenses possess interference properties, that is, these lenses have a central maximum, as well as secondary maxima and minima. The width of the central maxima approximates the diameter of the radiation transfer channel, e.g., the capillary diameter. A total intensity in the central maximum is directly proportional to $(N_c)^2$, where $N_c$ is the number of capillaries in the lens. Thus, such lenses can be efficiently used for obtaining information on the object, wherein defects are located.

When, e.g., the detect shadows N capillaries, the intensity in the central maximum becomes nearly proportional to $(N_c - N_q)^2$. This quadratic relation enables one to observe very efficaciously even minor defects in the object. For instance, while scanning various areas in the object and then subtracting the values of intensity in the central maxima from one another (the so-called "subtraction method"), one can easily locate the presence of the defect and its locally High energy resolution can be attained with the use of an embodiment of the device wherein the means for placing the object or sample is followed by a lens having axial symmetry. Such a lens is capable of energy resolution at a very high level. For instance, if it is necessary to attain an energy resolution on the lens optical axis to a certain level $\Delta E$ near a certain energy E, a spatial resolution $\Delta f = \Delta E/E$ corresponds to the noted energy resolution, where f is the lens focal length for the energy E.

In an embodiment of the device adapted for use in science and analytical instruments and devices, X-ray beams are used for receiving information about the elementary composition of the specimen. In a fluorescence analysis, a primary X-ray beam excites characteristic lines and the elementary composition of the specimen is reproduced by the analysis of these lines. Two methods are used, as a rule, in this case, namely, precision dispersion analysis against wavelengths (since Bragg diffraction is used, or energy dispersion analysis, wherein the energy spectrum of secondary particles is measured) or energy dispersive analysis with semiconductor detector.

In both cases, use of the lenses of the present device offers advantages. For example, when performing diffraction measurements, wherein X-rays generated by an X-ray tube are used as the original beam, a loss in the radiation intensity by 6–7 orders of magnitude occurs. This relates to the fact that only those photons are used which meet the Bragg law, equivalently, the photons should feature a divergence of from $10^{-3}$ to $10^{-4}$ rad depending on the type of crystal used.

Tomographs have gained a very widespread application in modern diagnosis, though they suffer from a number of disadvantages inherent therein, namely, high exposure dose and a spatial resolution often far from adequate, these disadvantages being related. For instance, if one tries to enhance the resolution twice-, the exposure dose has to be increased 16-fold. That is why the resolution value from one to a few millimeters is common in current tomographs.

It is a routine practice to use a continuous spectrum of bremsstrahlung, This is accompanied by the onset of the so-called "hardness effect", wherein harder photons are absorbed in the object to a lesser extent than softer ones. Because of this, some difficulties are encountered during image reconstruction, especially at the bone-muscle boundary These difficulties can be overcome by using the present device In this case, the tomograph layout may be the same as in the second-generation tomographs, that is, the radiation source is placed before the patient, while positioned there behind are an image-reducing lens and a detector (i.e., the sensor of the image-forming means) The patient is immovable, while the radiation source, the lens, and the detector are rigidly interlinked and together scan the patient's body.

In order to avoid the "hardness effect," the source-emitted radiation can be monochromatized by resorting to various techniques. For instance, a hemilens may be positioned past the radiation sources and an assembly of parallel capillaries be placed past the hemilens, while the entrance angle of the radiation emerging from the hernilens to the assembly is adjustable, thereby rendering adjustable the radiation spectrum.

In the present-day tomographs, the density distribution is judged by registering the radiation running from the source to a the radiation detector In this case, in order to gain information on the density distribution in one cut or another, a great number of exposures (as a rule, over one hundred) of the section should be carried out at different angles, the exposure dose being usually as high as 1 R or over. The situation may be improved upon if one registers the Compton scattering at the place under examination of the object concurrently with registering the radiation absorption.

Mammographs are used for the breast cancer diagnostics. Use of hemilens, ensuring the divergency of the order of $10^{-4}$ radian on the object, allows the increasing of spatial resolution. Besides it is no necessity in use of the antiscattering grids. Placing the detector far from patient (at the distance $\geq 50$ cm) permits the increase of contrast.

To this end the focal point of the X-ray lens is aimed at the place under examination. To the same focus is oriented another system of lenses (or collimators) rigidly coupled to the former X-ray lens. Such a system is able to scan the object in three directions. The second system of lenses mentioned before is associated with detectors capable of registering the Compton scattering. Another system of detectors is positioned past the object opposite the first lens in order to register the absorption of radiation. Such a system of tomography is assessed to provide a better resolution at a lower exposure dose. The layout of the device carrying this method into effect is similar to that depicted in FIG. 17.

Practical application of the proposed device in medical diagnosis can result in a drastically reduced exposure dose and high spatial resolution. Reduction of the exposure dose can be attained by virtue of filtering quasi-parallel radiation, as well as the possibility of image transfer involving a size reduction of the object being examined.

X-ray screens, intensifying screens, vidicons, etc., have an imagery threshold, which varies depending on the screen type, energy of photons, etc. Here and hereinafter said threshold is assumed to be $n=10^8$ photon/cm$^2$.

The object is irradiated by a parallel beam of photons. Located past the object is a lens (or a train of lenses) adapted to focus the radiation, and situated behind the lens or train of lenses is a screen. In the proposed device the entrance-to-exit diameter ratio may be 100:1.

Such being the case, to provide efficient focusing, the original beam divergence $\delta\theta$ must be $\delta\theta/\theta_c = d_1/d_0$, that is, if $d_1/d_0 = 100$, $\delta\theta/\theta_c$ should be on the order of $10^{-2}$; with $E=20$ keV, $\theta_c = 2 \cdot 10^{-3}$ rad, i.e. with the dimensions diminished by a factor of 100, $\delta\theta = 2 \cdot 10^{-5}$ rad. In this case, the exit area of a single capillary is reduced $10^4$ times. With such a focusing, as little as half the amount of photons that have transversed to the exit butt end of the lens are incident on the screen.

In this particular case, the number of photons necessary for imagery threshold is reduced by a factor of $0.5 \cdot 10^4$. This means that in the case where a lens is provided behind the object the number of photons incident on the object may be reduced by a factor of 5000. It is necessary at the same time to obtain good spatial resolution. As the resolution is two or three times the capillary entrance diameter, so to provide a 100-micron resolution, the capillary diameter should be of the order of 30 microns. In this case, with the dimensions reduced by a factor of 100, the capillary exit diameter should be of the order of 0.3 micron. The angle of convergence (or cone angle) of the capillaries is of the order of $2 \cdot 10^{-5}$ rad, and the lens length will be about 75 cm provided that the lens is composed of a plurality of capillaries or polycapillaries. There are two restrictions imposed upon the minimum size of a capillary, one of them being associated with diffraction and is independent of the energy of photons. The first is that the limit size should be $C/\omega_p = 100$ Å, where C is the velocity of light and $\omega_p$ is the plasma (Langmuir) frequency. The aforesaid limit is small can be neglected in this particular case The other restriction is concerned with the physical imaging process. The energy of photons is transformed on the screen of the image-forming means, i.e., in the detector, into the energy of electrons which, when dissipated, establish light quanta which produce the image of an object.

Maximum resolution in this case is associated with the range of path of electrons, and is approximately equal to about 10 microns Let $S_1$ denote a minimum area of the capillaries at the exit end before the screen, this area depending on the final range of electrons $S_1 = (10 \mu m)^2 = 10^{-6}$ cm$^2$. With the entrance area of the capillaries equal to $S_0$, the exposure dose reduction J will be $J = aS_0/S_1$, where a is the loss of radiation when transferred through a converging capillary, this loss being generally equal to ½, With $S_0 = 10^{-2}$ cm$^2$, J=5000.

A minimum resolution I equals the capillary entrance diameter multiplied by a factor of the order of 3, that is I =0.3 mm in this particular case.

Thus, as $S_0$ increases, J increases too, but I decreases inversely proportional to an increase in $S_0$.

In cases where a small-size image is to be produced, J decreases, because it is necessary to use the capillaries having small entrance diameters. For instance, when it is necessary to attain the resolution of an image of a tumor about 1 mm in size, it is necessary to use the capillaries having a diameter of about 0.3 mm, with J=500. Accordingly, for a tumor sized 0.3 mm, J=50.

A peculiar feature of the construction inherent in at least one of the lenses of the optical system used in the proposed device (and whenever the optical system has a single lens, inherent in the single lens), resides, as it has been stated hereinbefore in the disclosure of the present inventions, in the provision of the radiation transfer channels arranged in an orderly fashion across the lens with a due observation of axial symmetry. Such a peculiar feature is inherent in the construction of the present lens also when the lens is used per se or as a component of any other devices wherein fluxes of neutral or charged particles are to be converted.

Figure 18:
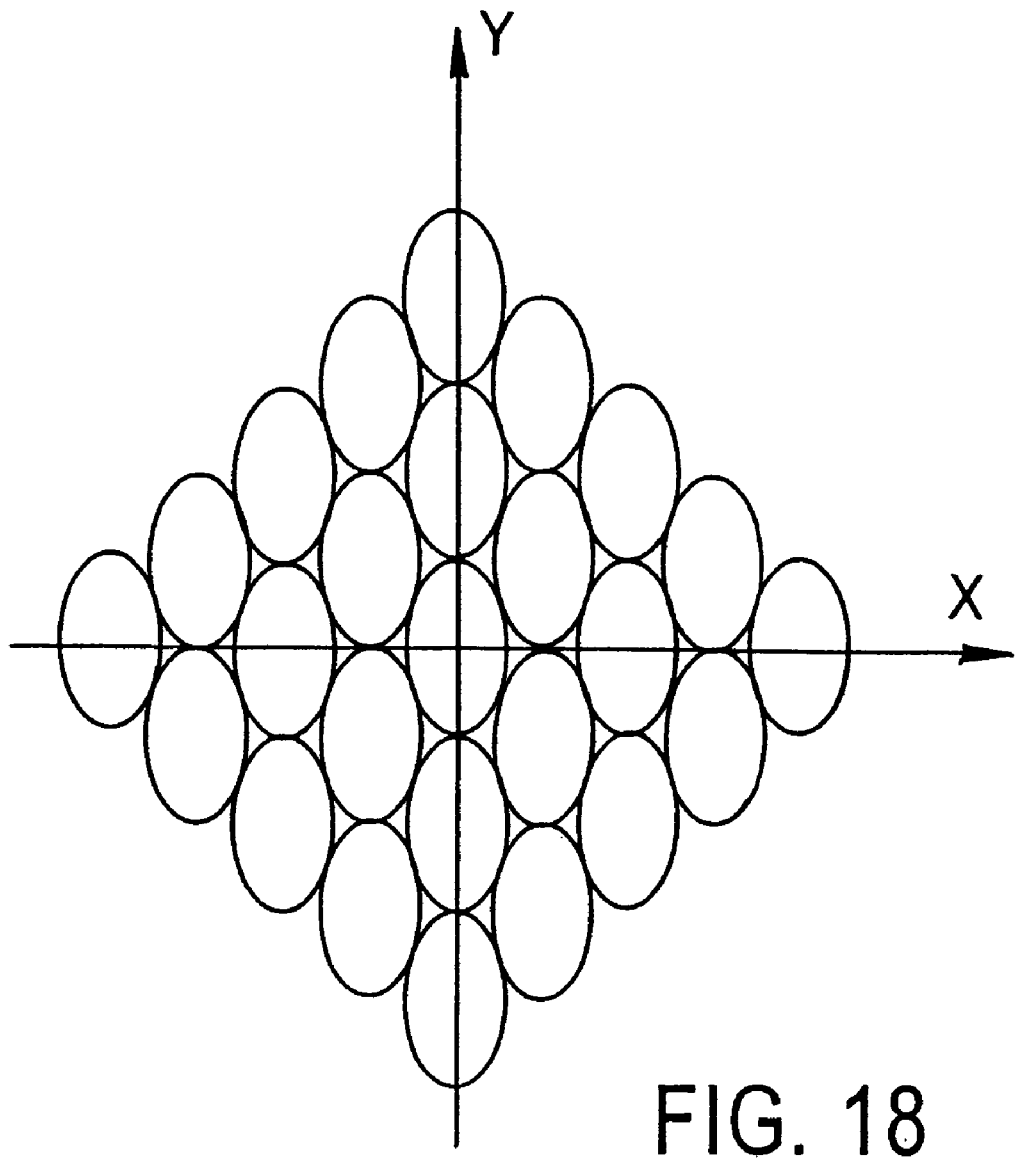
FIG. 18 shows an ordered structure of channels in the lens cross section featuring a mirror symmetry with respect to two axes, as well as a central and a rotational symmetry.

FIG. 18 illustrates an ordered arrangement of the lens channels, wherein a mirror symmetry with respect to cross-sectional axes x and y occurs. In this particular case, there occurs concurrently a central symmetry with respect to the lens longitudinal axis which passes square with the plane of the drawing through the point of intersection of the x and y axes any element under examination corresponds to the same element lying on a straight line passing through said element and this point on the other side of the center of symmetry at the same distance therefrom as the element under examination.

Apart from that stated above. FIG. 18 shows a axial symmetry with respect to the same axis as the central symmetry, that is, when rotated about the axis through 180° the figure shown in the drawing coincides with itself.

Figure 19:
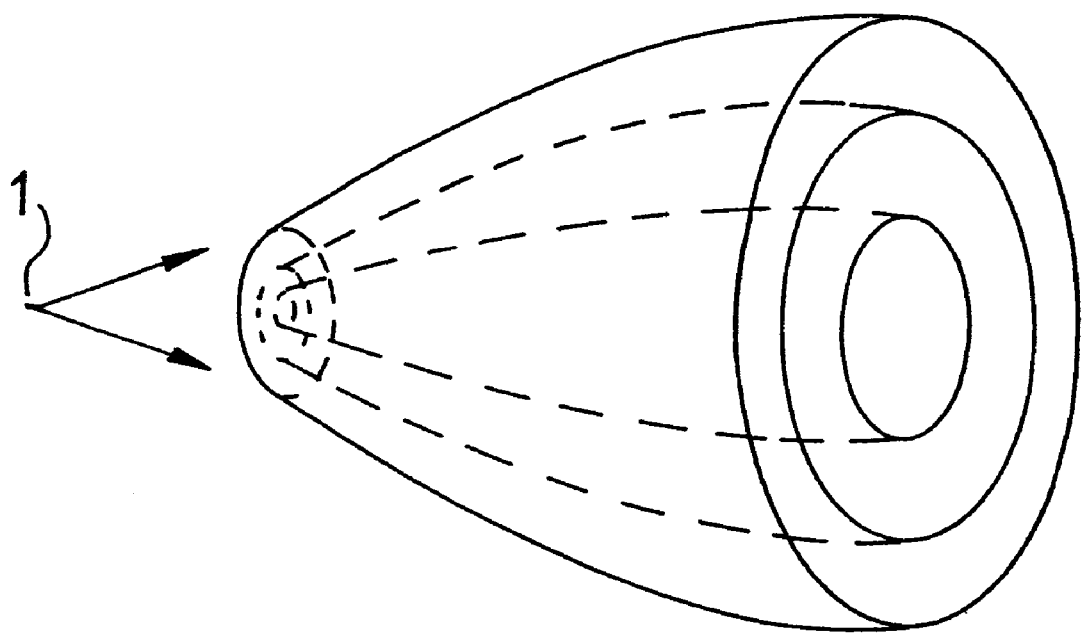
FIG. 19 shows an integrated lens in case, when it consists of sublenses of the highest degree of integration, which will derivate several coaxial layers.

FIG. 19 illustrates embodiment of an integrated lens in case, when it consists of sublenses of the highest degree of integration, which will derivate several coaxial layers.

Figure 20:
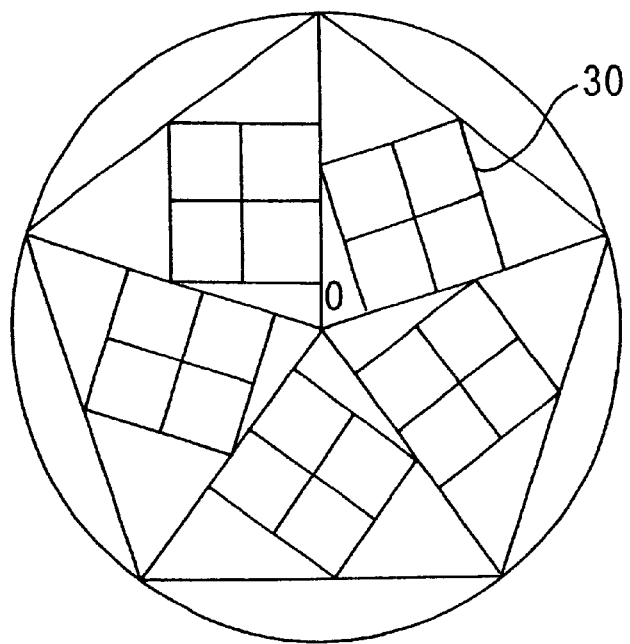
FIG. 20 shows a cross-sectional lens structure possessing a rotational symmetry alone.

FIG. 20 explains concept of a rotational symmetry. On it schematic is shown an ordered arrangement of square channels across the lens, with due observance of a rotational symmetry when rotated through an angle of $2\pi/5$ or a multiple thereof about the lens' longitudinal axis (passing through the point O square with the plane of the drawing), the figure shown in the drawing coincides with itself, in particular, each group 30 of the channels is coincident with a similar group.

Figure 21:
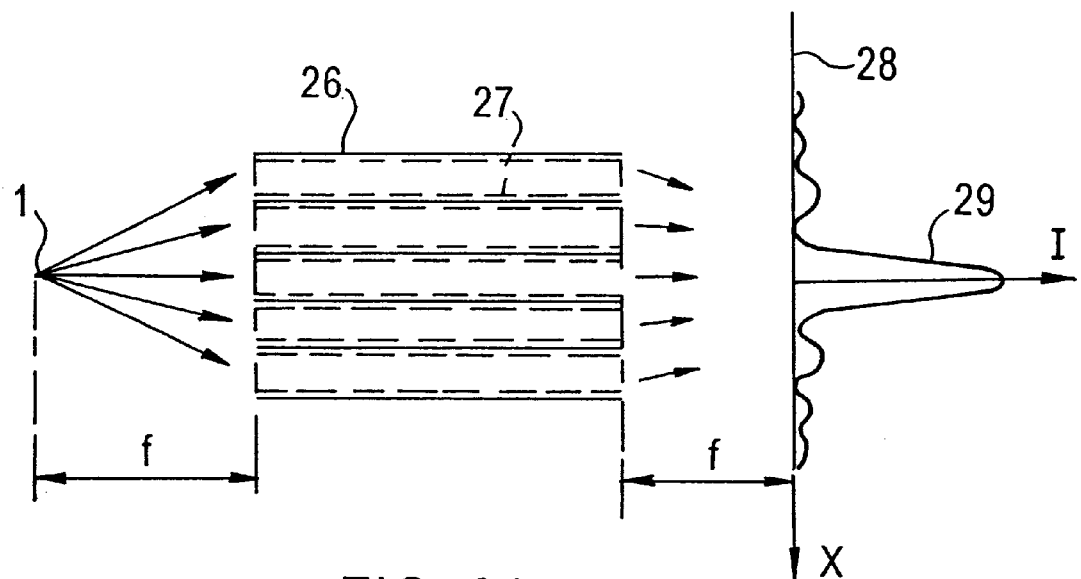
FIG. 21 shows the use of a set of parallel straight capillaries as a lens, as well as distribution of the intensity of emergent radiation in the focal plane.
Figure 22:
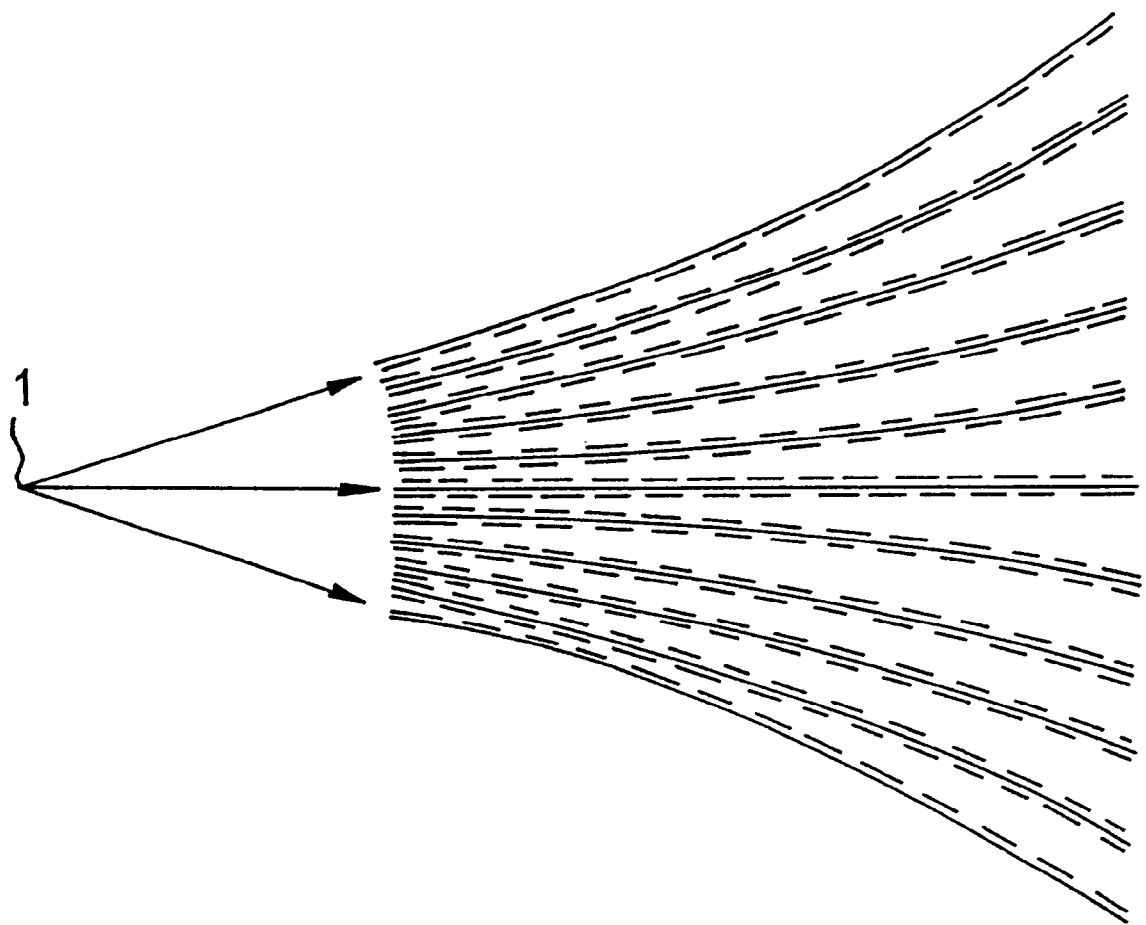
FIG. 22 is a view of a funnel-shaped lens having a concave lateral surface.
Figure 23:
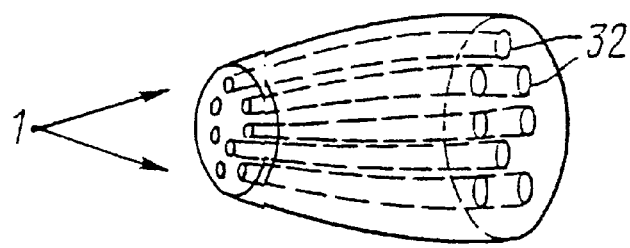
FIG. 23 is a view of an integrated lens, derivated by sublenses, having the round cross section.
Figure 24:
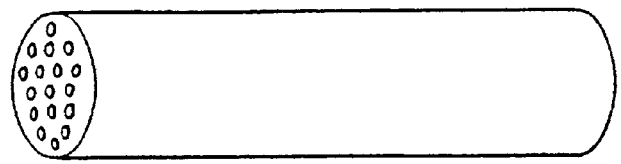
FIG. 24 is a view of a sublens of the least degree of integration consisting of capillary tubes, enclosed by an envelope.
Figure 25:
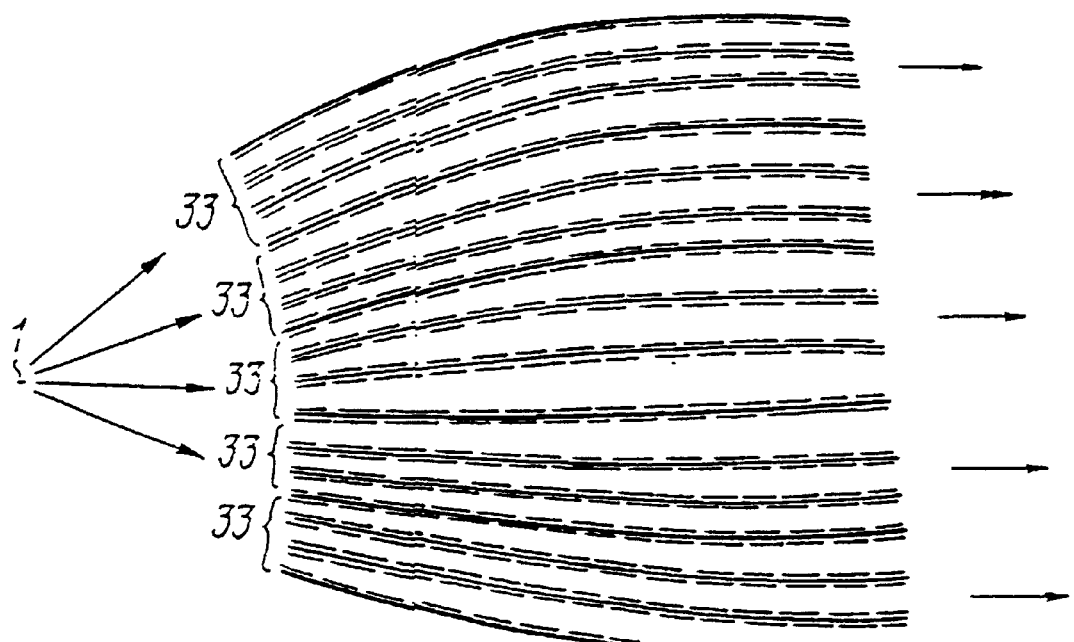
FIG. 25 is a view of a lens in the form of a set (or assembly) of sublenses.
Figure 26:
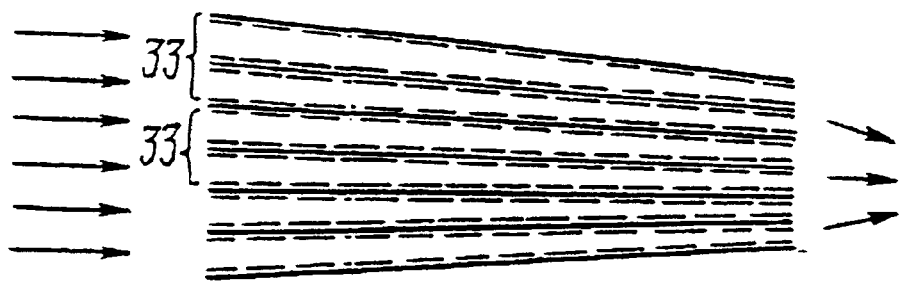
FIG. 26 is a view of a conical lens made with the use of sublenses.

As has been stated, provision made in the lens for channels arranged in an orderly fashion across it with the observance of axial symmetry brings about prerequisites for the onset of interference phenomena for the particles emerging from the lens. This enables one to efficiently focus the radiation even in the simplest embodiment of the lens, i.e., in the form of an assembly 26 (FIG. 21) built up of straight parallel capillaries (the so-called "capillary bars" or "capillary structure"). Indicated with dashed lines in FIG. 21 and in a number of figures described hereinafter are coatings applied to the walls of the radiation transfer channels. Depending on the length of the assembly 26, there may occur a single-, double-, or multiple reflection in each of the channels 27 The result is an interference pattern arising in a focal plane 28 which is spaced the same distance apart from the lens exit end as the radiation source 1 is spaced apart from the lens entrance end. This interference pattern corresponds to a graph 29 (FIG. 21) of radiation intensity I vs. x. This graph features a width of the principal maximum which is approximately equal to the diameter of an individual channel.

Of the same order of magnitude is the size of the focal spot in another embodiment of the lens featuring orderly arranged channels across it with observance of axial symmetry. It is noteworthy, for the sake of comparison, that, in the absence of interference phenomena, the size of the focal spot is of the following order of magnitude:

$$I_f = d + 2\theta_c f,$$

where d is the cross-sectional dimension of an individual channel, f is the focal length, and $\theta_c$ is the critical angle of external reflection.

For example, with the particle energy E=8 keV, the $\theta_c$ is on the order of $3 \cdot 10^{-3}$ rad. With a typical value of f=110 cm, the following expression holds true $I_f = d + 0.6$ mm, i.e., a degree of focusing better than 0.6 mm is unattainable even when the channels are build up of very fine capillaries. A provision of interference conditions in the proposed lens makes it possible to overcome this restriction, with the result that the degree of focusing happens to be dependent on the channel diameter alone.

Performance capabilities of the proposed integrated lens are provided due to interference, and are combined with technological merits inherent in the construction of the integrated lens.

At the more detail consideration the integrated lens is the package of sublenses of a various degree of integration, wherein the sublens of the least degree of integration represents the package in a common envelope of radiation transporting channels in form of microcapillary tubes, which is growing out of their drawing and reduction together with an envelope at the temperature of a softening of their material. The sublens of each higher degree of integration represents the package in a common envelope of the sublenses of the previous degree of integration, which is growing out of their drawing and reduction together with an envelope at the temperature of softening of their material. All sublenses of the highest degree of integration are composed in a unified structure which is growing out of joint forming at the temperature of softening of their material. Thus the channels of radiation transporting, with the exception of the channels, located near to the longitudinal axis of lens, are made with a capability, at least, of double full external reflection of radiation during its transporting and with increase of quantity of reflections for channels removed from the longitudinal axis of a lens. The channels located near to this axis are made with a capability of transporting the radiation at single full external reflection or without it.

All sublenses of the highest degree of integration can be made in a common envelope, which is an external envelope of an integrated lens.

The channels located near to the longitudinal axis of integrated lens have smaller length in comparison with other ones or exceed their cross-sectional sizes for transporting radiation in them at single full external reflection or without it.

Technology of integrated lens making consists of several stages. At the first stage, glass or metal tubes of several centimetres diameter are drawing in the furnace at the softening temperature of their material. As a result, the reduction of cross section of tubes up to 0.5–1 mm takes place, i.e. one obtains a small size tubes—capillaries. At the second stage, a number of capillaries ($\geq 1000$) are inserted in the common envelope from the same material and this package is drawing in furnace at the softening temperature; it results in reduction of every capillary's cross section and in decreasing the whole package cross section size. Obtained package is the sublens of the least degree of integration. At the third stage, operations, analogous to the foregoing ones (see second stage), are carried out in relation to the sublenses of the least degree of integration inserted in a common envelope The sublenses of the second degree of integration results from this stage.

Such stages may be continued for making the sublenses of third and more higher degree of integration. Integrated lens from the sublenses of required degree of integration one obtains at the final stage, wherein the package of the mentioned sublenses is forming at the material softening temperature for obtaining the integrated lens with required law of changing the cross section along the length. This final stage, in particular, may be carried also with package of the sublenses inserted in a common envelope, that is simultaneously tne external envelope of integrated lens.

The above mentioned operation of drawing is performed by fixing the upper part of tubes or sublenses and hanging the weight from its lower part.

Typical temperature of boronsilicate glasses is 550° C. approximately, and of quartz glasses is of the order of 1000° C.

Finally, the size of channel cross section in an integrated lens may be of micron or submicron level, i.e., much lesser than the size of cross section of capillaries, making at the first stage of manufacturing technology. So the channels of integrated lens may be called microcapillaries.

Figure 27:
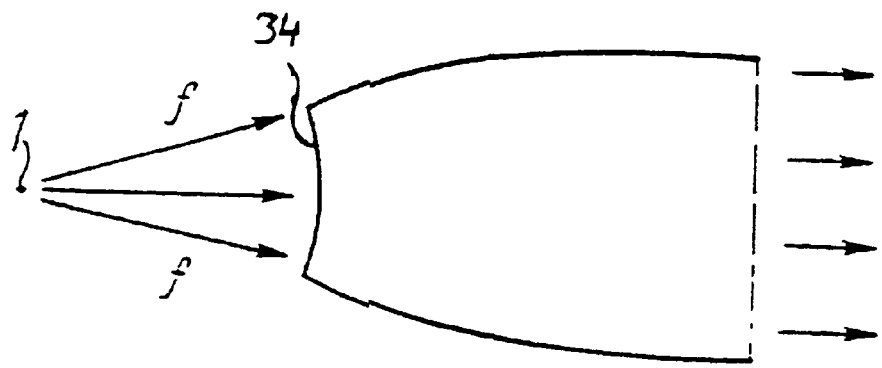
FIG. 27 is a view of a lens (hemilens) shaped as a half-barrel and adapted for transforming diverging radiation into quasi-parallel radiation (or for focusing quasi-parallel radiation)

FIG. 27 shows a half-barrel-shaped hemilens for transforming a diverging radiation emitted by the source 1 into quasi-parallel form. An entrance end 34 of the hemilens is concave so as to provide a uniform intensity of the emergent beam within its cross-section.

Figure 28:
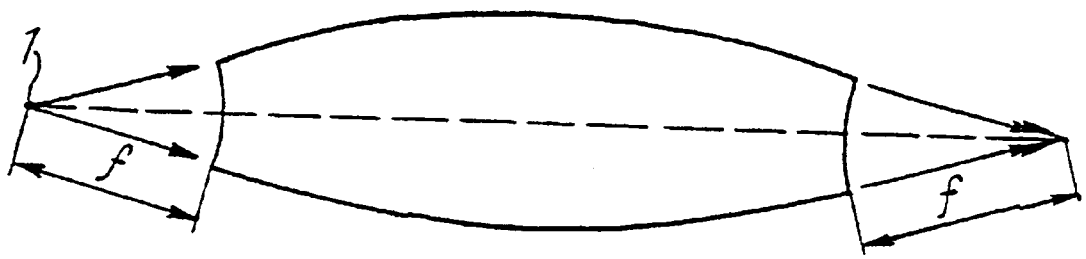
FIG. 28 is a view of a barrel-shaped lens for focusing diverging radiation.
Figure 29:
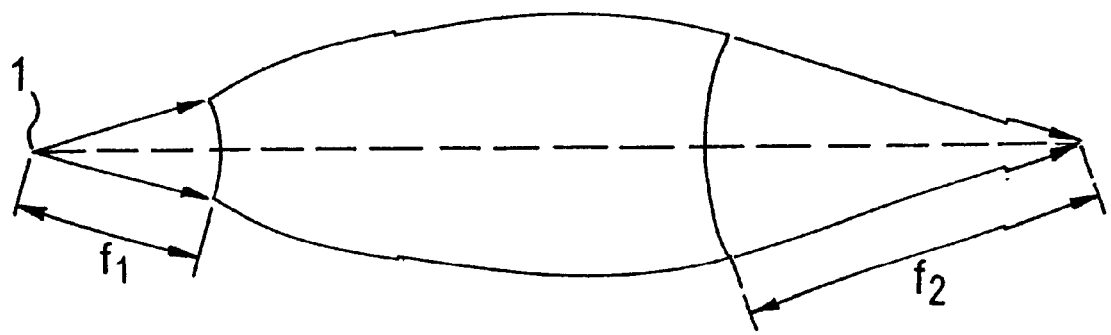
FIGS. 29 and 30 depict asymmetrical lenses for focusing a diverging radiation, these lenses featuring a constant and a variable bending radius of the channels, respectively, in a longitudinal lens section.
Figure 30:
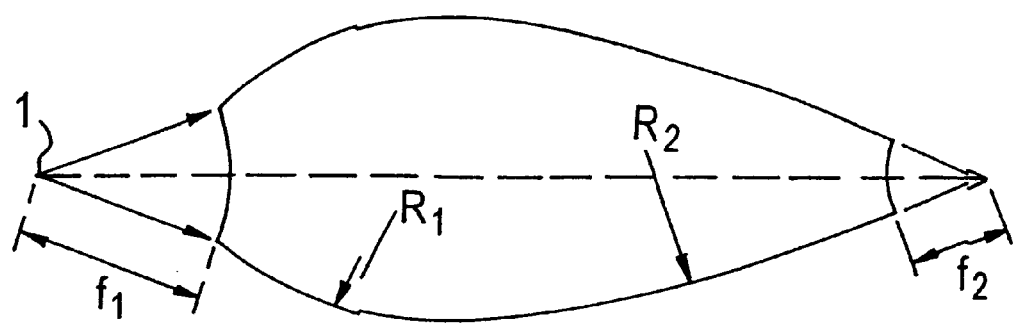

FIGS. 27, 28–30 present a barrel-shaped symmetrical lens and a barrel-shaped asymmetrical lens, both adapted for focusing a diverging radiation emitted by the source 1. When the symmetrical lens of FIG. 28 is used, the radiation is focused at a distance f from the exit end thereof, which is equal to a distance between the radiation source 1 and the lens' entrance end. For the lenses of FIGS. 29 and 30, the distances mentioned above differ from each other, being equal to $f_2$ and $f_1$, respectively. The lens of FIG. 28 includes channels having the same radius of bending throughout the entire length thereof, whereas the radiation transfer channels in the lens of FIG. 30 have their right-hand portion bent at a radius $R_2$ which is different than a radius $R_1$ at which the left-hand portion of the channels are bent. There may even be a lens which is asymmetrical in a longitudinal section, wherein the channels have a variable bending radius changing monotonically. A lens with bent channels may also be shaped as a flare or funnel (FIG. 31), in this case the lens' side surface, unlike the lenses of FIGS. 27–30, is concave rather than convex. Such a lens may be used for producing an enlarged image of the object located before the lens entrance end (when a quasi-pointlike radiation source is used). The accuracy of the resultant image is approximately equal to the cross-sectional dimension of the channel at the lens entrance.

Apart from the fact that the current lens may have channels arranged in an orderly fashion in its cross-section in the sense discussed before, each "layer" of the channels has, as a rule, its own bending radius and hence its own length. Here the layers of channels are understood to mean groups of channels establishing closed contours, in particular, having in cross section a kind of rings, as shown in FIG. 19. The layers may also not establish closed contours, e.g., be "flat", which is the case when the lens has a rectangular cross-section, these layers having the same width as the cross-section. For each of such layers located one side of the plane of symmetry of the lens, i.e., the plane passing through the lens' longitudinal axis, a similar symmetrically arranged layer should occur on the other side of the plane. In a cross-sectional view of the lens, the channels forming such layers are symmetrical with respect to the axis of the cross-section. That is why monochromatic photons undergo unequal number of reflections in various channels. In this way, a system of waves differing in phase arises after the photons have emerged from the lens (considering the process from the standpoint of the wave theory). A phase difference is established due to different photon path lengths along the channels when the channels are arranged randomly, no useful effects are produced. But in the case of axial symmetry, this results, as has been stated before, in wave interference. Of practical importance is the fact that a considerable proportion of energy emerging from the lens is concentrated in the central maximum, and the size of the central interference spot is found to approximate the cross-sectional dimension of a radiation transfer channel.

When manufacturing the capillary lenses and hemilenses, the capillary may be so drawn as to be twisted, and the paths of photons may resemble a helical line. It is possible that one pan of the capillaries "turns" in one sense, and another part turns in the opposite sense. This enables one to obtain a number of interesting capabilities. First, if a beam of unpolarized photons (or neutrons, or charged particles) is applied to the lens entrance, the beam can be subdivided, by virtue of the twist effect, into a number of plane-polarized beams. Second, when a plane-polarized beam is originally provided, the plane of polarization of the beam rotates in a twisted capillary.

Some further possibilities are opened up due to depositing coating upon the walls of the radiation transfer channels. This may be done in order to provide diffuse and potential scattering or interference of the radiation being transferred It may occur on the multilayer structures formed by the coatings and the channel walls (the presence of such coatings being shown schematically with the dashed lines FIGS. 21, 25, 26 and 22. In the last figure a funnel-shaped lens having a concave lateral surface is shown).

In order to cut off the soft portion of the spectrum so as to obtain a quasimonochromatic spectrum from a complex spectrum, the channel walls may be coated by a material which absorbs the spectral portion efficiently.

The fact that the coatings are layered makes it possible not only to transfer the radiation but also to selectively choose a portion thereof. It is due to the resultant interference that the critical angle of reflection and the reflection factor are very much increased, this phenomenon occurring inside the channels.

The presence of a small transition layer can, in many cases, serve to increase the lens efficiency to a great extent. For instance, when transferring neutrons, the layer can be ferromagnetic, whereby the angle of reflection is increased. When transferring charged particles, the layer can be crystalline, whereby reflection occurs in a way resembling channeling of particles in crystals.

Coating the dielectric substrate with a metallic layer makes possible the "channeling" of the charged particles through such a medium In the reverse case, the dielectric is charged to prevent, by its charge, "channeling" of particles.

In this case, the substrate and the reflecting surface differ in their properties because the latter is a metallic layer.

When use is made of multiple reflections of radiation on alternating media differing in physical properties and the resultant scattering, a possibility arises for efficiently controlling the radiation.

The lenses utilizing the combination may be widely implemented in diverse fields of engineering. In particular, use can be made of a set of rectangular or square capillaries so coated by a multilayer structure that the period of the structure alternates, thus establishing, after reflection, two different quasimonochromatic beams similar space-oriented.

The critical angle of reflection of neutrons in a layer, where a magnetic field is present, is determined from the following formula:

$$\theta_c = \lambda [N\bar{b}/\pi \pm (m/2\pi^2\hbar^2)\mu B]^{1/2},$$

where N is the nuclear density, $\lambda$ is the neutron wavelength, $\bar{b}$ is the nuclear coherent-scattering amplitude, $\mu$ is the neutron magnetic moment, m is the neutron mass, B is the magnetic induction, and $\hbar$ is the Planck's constant The presence of two signs, plus and minus, and hence two angles, relates to the two possible polarizations of the neutron spin.

With high-strength magnetic fields, when $N\bar{b} \leq (m/2\pi^2)\mu B$, a single critical angle of reflection is observed. In this case, totally reflected neutrons are polarized.

Therefore, when establishing, e.g., two- or three-dimensional structures having a magnetic reflecting surface, the user can control not only the paths but also polarization of neutrons.

Alternating media can be established, wherein the reflecting medium is a magnetic mirror, e.g., a thin cobalt mirror. Using alternating media differing in magnetic properties, one can increase the critical angle of reflection without decreasing the reflection factor.

Industrial Applicability

The present invention finds application in analytical instrument-making, more specifically, in elementary analysis, three-dimensional local analysis, defectoscopy, ecological monitoring, the establishment of tomographs with micro and submicron resolution, the development of high-efficiency and intensity microscopes in microscopy (in particular, in microscopic examinations of biological objects), contact and projection lithography in microelectronics, X-ray and neutron diffractometry for developing new-type collimators (as new-type diffraction and interference instruments), in particular, for enhancing the density of radiation.

What is claimed is:

1. A device for producing an image of an object, comprising:

a source of radiation which appears as a flux of particles, means for placing the object such that said object may be exposed to the effect of radiation generated by said source, means for image formation for registering the distribution of intensity of radiation after the radiation interacts with the object, and an optical system which incorporates at least one integrated lens converting said flux of particles and is interposed between said radiation source and said means for placing the object or between said means for placing the object and the image forming means, said integrated lens is a package of sublenses of a various degree of integration, wherein the sublens of least degree of integration represents the package in a common envelope of radiation transporting channels in form of microcapillary tubes, which is growing using drawing and reduction together with an envelope at the temperature of a softening of their material, the sublens of each higher degree of integration represents the package in a common envelope of the sublenses of previous degree of integration, which is growing using drawing and reduction together with an envelope at the temperature of a softening of their material, all sublenses of highest degree of integration are composed in a unified structure which is growing using joint forming at the temperature of a softening of their material, and the channels of radiation transporting, with the exception of the channels located near longitudinal axis of lens, are made with a capability, at least, of double full external reflection of radiation during radiation transporting and with increase of quantity of reflections for channels removed from the longitudinal axis of a lens, the channels located near the longitudinal axis are made with a capability of transporting the radiation at single full external reflection or without reflection.

2. The device according to claim 1, wherein all sublenses of the highest degree of integration are inserted in a common envelope, which is an external envelope of an integrated lens.

3. The device according to claim 1 or claim 2, wherein the channels, located near the longitudinal axis of the integrated lens, for transporting radiation at single full external reflection or without reflection, have smaller length in comparison with other ones.

4. The device according to claim 1 or claim 2, wherein the channels located near to the longitudinal axis of the integrated lens, for transporting radiation at single full external reflection or without reflection exceed other ones by the cross-sectional sizes.

5. The device according to claim 1, wherein said image-forming means is so positioned that the radiation transmitted through the object can be transferred to said image-forming means.

6. The device according to claim 5, wherein said optical system comprises a plurality of asymmetrical lenses interposed between the means for placing the object and said image-forming means, said asymmetrical lenses being so assembled as to transfer the radiation emerging from different elements of the object.

7. The device according to claim 5, wherein said optical system comprises a diverging hemilens composed of a conical capillary structure interposed between the means for placing the object and said image-forming means so as to enlarge the image of the object.

8. The device according to claim 7, wherein said optical system further comprises a second diverging lens composed of conical capillary structure, said second diverging lens having a smaller cross-sectional dimension than the first lens, said second lens being interposed between the radiation source and said means for placing the object.

9. The device according to claim 5, wherein said optical system further comprises a lens system for forming a quasi-parallel beam of particles, said lens system being interposed between the radiation source and said means for placing the object.

10. The device of claim 9, wherein the radiation source forms two characteristic $K_\alpha$ spectral lines, and said optical system further comprises a rotary filter-window having two alternating sectors for suppressing the radiation of either of the $K_\alpha$ spectral lines, said lens system having longitudinal axis.

11. The device of claim 9, wherein the radiation source forms forming two characteristic $K_\alpha$ spectral lines, said optical system further comprising an alternate lens system for forming a quasi-parallel beam out-of-parallel to a first beam, and two crystal-monochromators for discriminating either of the two $K_\alpha$ spectral lines, said crystal monochromators being located past their respective lens systems so as to reflect monochromatized beams towards said means for placing the object the device further comprising:
    at least one shield for preventing the radiation generated by the source from being directly incident upon said means for placing the object and
    a second image-forming means, each of said image-forming means located past said means for placing the object so as to register the distribution of intensity of the radiation passed through the object and reflected from the crystal monochromators.

12. The device according to claim 5, wherein said lens interposed between the radiation source and the means for placing the object, focuses the radiation inside the object.

13. The device according to any one of claim 1, wherein the image-forming means is so positioned that a secondary radiation from substance of the object due to interaction of said substance with the source-generated radiation can be transferred to said image-forming means.

14. The device according to claim 13, wherein the radiation source forms a flux of charged particles for exciting a secondary X-radiation in the substance of the object and the optical system further comprises a hemilens for transferring said secondary radiation to the image-forming means and scanning the object with the focal point of said hemilens.

15. The device according to claim 13, wherein the optical system comprises a lens for transferring radiation generated by the source to the means for placing the object, and a lens for transferring the radiation to the image-forming means, both said lens having a common focal point.

16. The device according to claim 15, wherein a beam monochromatization means is interposed between the lens for transferring the secondary radiation to said image-forming means, and said image-forming means.

17. The device according to claim 15, wherein a polarizing target is interposed between the lens for transferring the source-generated radiation to the means for placing the object and said means for placing the object, said target being provided for changing the direction of the beam reflected therefrom by 90° with respect to the beam incident thereon.

18. The device according to claim 17, wherein the polarizing target is a crystal monochromator.

19. The device according to claim 13, wherein said optical system providing formation of a quasi-parallel beam, further comprising a collimator having a system of straight capillaries, and interposed between the means for placing the object and the image-forming means, a first lens, said collimator, said image-forming means being disposed in same half-space as the means for placing the object.

20. The device according to claim 13, wherein said lens is provided for focusing the radiation inside the object, further comprising a collimator having a system of cone-shaped capillaries, said collimator being focused at the same point as said lens and interposed between the means for placing the object and the image-forming means, the collimator, said image-forming means being situated in the same half-space with respect to the means for placing the object.

21. The device according to claim 13, wherein the radiation source forms quasi-parallel plane-polarized radiation, and the optical system comprises:

a first lens for focusing the plane-polarized radiation composed of a square capillary structure, said first lens being interposed between the radiation source and the means for placing the object for focusing the radiation inside the object, a second lens made up of cone-shaped capillaries and located before said image-forming means, said second lens having a common focal point with the first lens for forming plane-polarized radiation and an optical axis situated in the plane of vector of intensity of magnetic field of the radiation and arranged square with the optical axis of the first lens for focusing said plane-polarized radiation, and a third lens located on an extension of the optical axis of said first lens for focusing said plane-polarized radiation and having a common focal point therewith, said third lens being provided for forming quasi-parallel radiation, a second image-forming means positioned past the third lens.

22. The integrated lens for transformation of radiation representing a flow of neutral or charged particles, containing channels of transporting of radiation with full external reflection made as a package of sublenses of a various degree of integration, wherein the sublens of least degree of integration represents the package in a common envelope of radiation transporting channels in form of microcapillary tubes, which are growing together with an envelope at the temperature of softening of their material, the sublens of each higher degree of integration represents the package in a common envelope of the sublenses of previous degree of integration, which are growing together with an envelope at the temperature of softening of their material, all sublenses of highest degree of integration are composed in a unified structure which is growing out of joint forming at the temperature of softening of their material, and the channels of radiation transporting, with the exception of the channels located near the longitudinal axis of lens, are made with a capability, at least, of double full external reflection of radiation during radiation transporting and with increase of quantity of reflections for channels removed from the longitudinal axis of a lens, the channels located near to the longitudinal axis are made with a capability of transporting the radiation at single full external reflection or without reflection.

23. A lens according to claim 22, wherein all sublenses of the highest degree of integration are inserted in a common envelope, which is the external envelope of an integrated lens.

24. A lens according to claim 22, wherein the channels located near the longitudinal axis of the integrated lens, for transporting radiation at single full external reflection or without reflection have smaller length in comparison with other ones.

25. A lens according, to claim 22, wherein the channels located near the longitudinal axis of the integrated lens, for transporting radiation at single full external reflection or without reflection exceed other ones by the cross-sectional sizes.

* * * * *